United States Patent
Che et al.

(10) Patent No.: US 12,383,511 B2
(45) Date of Patent: Aug. 12, 2025

(54) OSTEOGENIC AGENTS AND USES THEREOF

(71) Applicant: GoldPorp Pharma Limited, Hong Kong (CN)

(72) Inventors: Chi-Ming Che, Hong Kong (CN);
Lai-King Sy, Hong Kong (CN);
Chun-Nam Lok, Hong Kong (CN);
Wai-Ping Lee, Hong Kong (CN)

(73) Assignee: GoldPorp Pharma Limited, Hong Kong (CN)

( * ) Notice: Subject to any disclaimer, the term of this patent is extended or adjusted under 35 U.S.C. 154(b) by 0 days.

(21) Appl. No.: 17/713,384

(22) Filed: Apr. 5, 2022

(65) Prior Publication Data

US 2023/0310342 A1 Oct. 5, 2023

(51) Int. Cl.
*A61K 31/015* (2006.01)
*A61P 19/10* (2006.01)

(52) U.S. Cl.
CPC ............ *A61K 31/015* (2013.01); *A61P 19/10* (2018.01)

(58) Field of Classification Search
CPC ................................ A61K 31/015; A61P 9/10
See application file for complete search history.

(56) References Cited

U.S. PATENT DOCUMENTS

2010/0092559 A1* 4/2010 Ellies ..................... A61K 31/16
514/284

FOREIGN PATENT DOCUMENTS

CN 102228573 A * 11/2011
KR 20140108796 A * 9/2014

OTHER PUBLICATIONS

Machine English Translation CN-102228573 A (Year: 2011).*
Machine English Translation KR-20140108796 A (Year: 2014).*
Wang et al. Juncus inhibits osteoclast formation induced by RANKL, Tianjin Medical Journal, 12, 2018, pp. 624-628. (Year: 2018).*
Yu-Che Chang, 2016, 104, 257, Studies on the Chemical Constituents and bioactivities of Juncus effusus. (Year: 2016).*
Toth et al. Journal of Natural Products, 2018, 81, 661-678. (Year: 2018).*

* cited by examiner

*Primary Examiner* — Kara R. McMillian
(74) *Attorney, Agent, or Firm* — George G. Wang; Bei & Ocean

(57) ABSTRACT

Compositions and methods for reducing, or inhibiting bone loss in a subject in need thereof have been developed. Pharmaceutical compositions including one or more osteogenic compounds, or functional derivatives thereof, in an effective amount to reduce, or inhibit bone loss, or promote bone formation, preferably via stimulation of osteoblast differentiation, are provided. The compositions are particularly suited for treating bone loss associated with osteoporosis. Methods for treating, or preventing bone loss using the composition, optionally in combination with one or more therapeutic, prophylactic or diagnostic agents, or procedures, are described.

12 Claims, 7 Drawing Sheets
Specification includes a Sequence Listing.

A  B

A

B

C

D

E

A

B

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Primer used for PCR

<400> SEQUENCE: 1
tcagggcaat gaggtcacat c                                              21

<210> SEQ ID NO 2
<211> LENGTH: 19
<212> TYPE: DNA
<213> ORGANISM: Artificial Sequence
<220> FEATURE:
<223> OTHER INFORMATION: Primer used for PCR

<400> SEQUENCE: 2
cacaatgccc acggacttc                                                 19

<210> SEQ ID NO 3
<211> LENGTH: 24
<212> TYPE: DNA
<213> ORGANISM: Artificial Sequence
<220> FEATURE:
<223> OTHER INFORMATION: Primer used for PCR

<400> SEQUENCE: 3
```

```
gcaataaggt agtgaacaga ctcc                                              24

<210> SEQ ID NO 4
<211> LENGTH: 21
<212> TYPE: DNA
<213> ORGANISM: Artificial Sequence
<220> FEATURE:
<223> OTHER INFORMATION: Primer used for PCR

<400> SEQUENCE: 4
gtttgtaggc ggtcttcaag c                                                 21

<210> SEQ ID NO 5
<211> LENGTH: 21
<212> TYPE: DNA
<213> ORGANISM: Artificial Sequence
<220> FEATURE:
<223> OTHER INFORMATION: Primer used for PCR

<400> SEQUENCE: 5
gatgccacag atgaggacct c                                                 21

<210> SEQ ID NO 6
<211> LENGTH: 20
<212> TYPE: DNA
<213> ORGANISM: Artificial Sequence
<220> FEATURE:
<223> OTHER INFORMATION: Primer used for PCR

<400> SEQUENCE: 6
ctgggcaaca gggatgacat                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer used for PCR

<400> SEQUENCE: 7
tggtgctgcc aaggctgtgg                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer used for PCR

<400> SEQUENCE: 8
tctccaggcg gcacgtcaga                                                   20
```

OSTEOGENIC AGENTS AND USES THEREOF

FIELD OF THE INVENTION

The invention generally relates to compositions and methods for treating, alleviating, or preventing bone loss, such as in osteoporosis.

BACKGROUND OF THE INVENTION

Osteoporosis is the most prevalent bone disease in the United States. It is characterized by accelerated bone loss which results in brittle and weak bones that are easily fractured. Bones are continuously regenerated with new bone replacing old bone. However, in older individuals this process is less efficient and more bone is lost than is replaced with new bone. This results in bones that are thinner and weaker. Patients with osteoporosis have an increased risk of fractures, particularly of the hip, spine, and wrist.

Osteoporosis often occurs as a result of an imbalance between bone formation (action of osteoblasts) and bone resorption (action of osteoclasts) during the remodeling process. Treatment for osteoporosis mainly aims at the prevention of fragility fractures, by reducing bone loss (anti-resorptive agents), or alternatively, by improving the bone density and strength (anabolic agents) (Khan, S N et al., *Clin Obstet Gynecol* 56, 694-702 (2013)). A number of currently used anti-osteoporotic agents act by inhibiting osteoclastic activity to reduce bone resorption. However, osteoporosis is a chronic disease, and prolonged treatment by anti-resorptives to suppress bone remodeling may lead to a failure of repair, to microcracks, and bone necrosis (Miller, P D et al., *Osteoporos Int.* 21, 1793-802 (2010)). Induction of osteogenesis is a more viable approach in the treatment and/or prevention of osteoporosis. Thus, effective therapies that progressively encourage bone formation by increasing osteoblast activity are urgently needed.

Despite many recent advances in understanding the mechanisms of bone loss associated with osteoporosis, an effective treatment for these conditions is still lacking.

A notable class of osteogenic agent is derived from the estrogen-like compounds from natural plant sources such as "phytoestrogen" (Poluzzi E et al., *Curr Med Chem.* 21, 417-36 (2014)). The application of phytoestrogen as osteogenic agent is related to the fact that endogenous estrogens regulate bone mass in postmenopausal women by maintaining balance of osteoblastic bone formation and osteoclastic bone resorption. Estrogen deficiency in the postmenopausal stage can result in enhanced bone resorption, leading to osteoporosis. While estrogen can be used to treat osteoporosis in postmenopausal women, it may also increase risk of breast and uterine cancer. However, phytoestrogens have an activity profile distinctively different from estrogen, and may therefore provide new therapeutic opportunities to osteoporosis.

Therefore, it is an object of the invention to provide new and effective therapeutic agents and methods for treating diseases and disorders associated with bone loss.

It is an objective to provide new methods and treatments to promote bone repair, formation by stimulating osteoblast differentiation, activity and survival.

BRIEF SUMMARY OF THE INVENTION

Pharmaceutical compositions including an effective amount of one or more osteogenic compounds, and methods of use thereof for treating, inhibiting, or preventing bone loss are disclosed. Typically, administration of the compositions is effective to reduce or inhibit bone loss in a subject in need thereof.

The disclosed compositions and methods are particularly effective for treating bone loss conditions such as osteopenia and osteoporosis. Compositions include one or more osteogenic molecules in an effective amount to stimulate osteoblast differentiation, osteoblast activities, and/or reduce osteoblast apoptosis, at/near the site of treatment. In some embodiments, the one or more osteogenic molecules are phenanthrenes, or derivatives thereof. In one embodiment, the composition consists essentially of effusol, or derivatives thereof.

Compositions and methods of use thereof for enhancing the rate of calcium deposition by osteoblasts into bone matrix are described. Preferably, the disclosed compositions and methods are also effective in reducing, or inhibiting bone resorption by osteoclasts at/near the site of treatment.

Compositions and methods of use thereof for enhancing osteogenic protein expression are described. Exemplary osteogenic proteins include alkaline phosphatase, osteocalcin, osteoportin, osteonectin, bone sialoprotein, and combinations thereof. Compositions and methods of use thereof for increasing the levels of osteoblast-specific transcription factors are described. Exemplary osteoblast-specific transcription factors include RUNX2, DLX5, SP7, and combinations thereof.

Compositions and methods of use thereof for increasing levels of phosphorylation of one or more mitogen-activated kinases (MAPKs) involved in the osteoblast differentiation are also described. Exemplary MAPKs include p38. Compositions and methods of use thereof for increasing protein expression, transcript level, and/or activity of one or more members of the Wnt/β-catenin signaling pathway are also described.

Methods of treating subjects in need there using these compositions are also provided. Typically, the disclosed compositions are administered systemically to the subject, preferably a human subject. In some embodiments, the compositions are administered prior to, in conjunction with, subsequent to, or alternation with additional therapy/procedure, for example, treatment with one or more therapeutic, prophylactic or diagnostic agent.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

over a period of 4 days; (B) the effect of F1 and F4 on cell viability in MC3T3-E1 osteoblasts.

Figure 2:
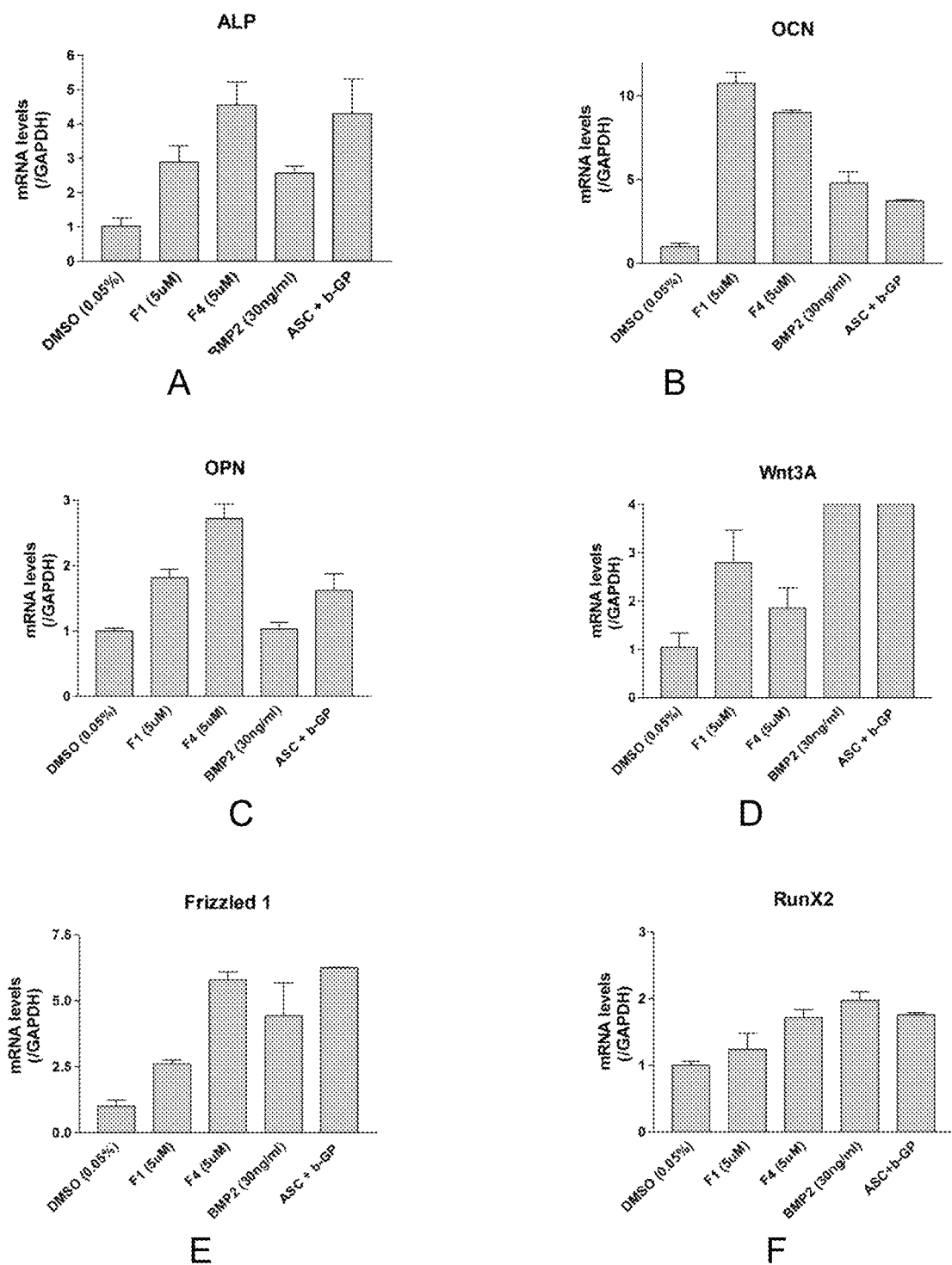

FIG. 2 is bar graphs showing mRNA levels of osteogenic genes related to osteoblastic differentiation determined by qPCR in MC3T3-E1 cells treated with 5 μM F1, 5 μM F4, 30 ng/mlBMP2, Ascorbate plus β-glycerophosphate, or 0.05% DMSO vehicle for a period of 4 days, including ALP (A), OCN (B), OPN (C), Wnt3A (D), Frizzled 1 (E), RunX2 (F).

Figure 3:
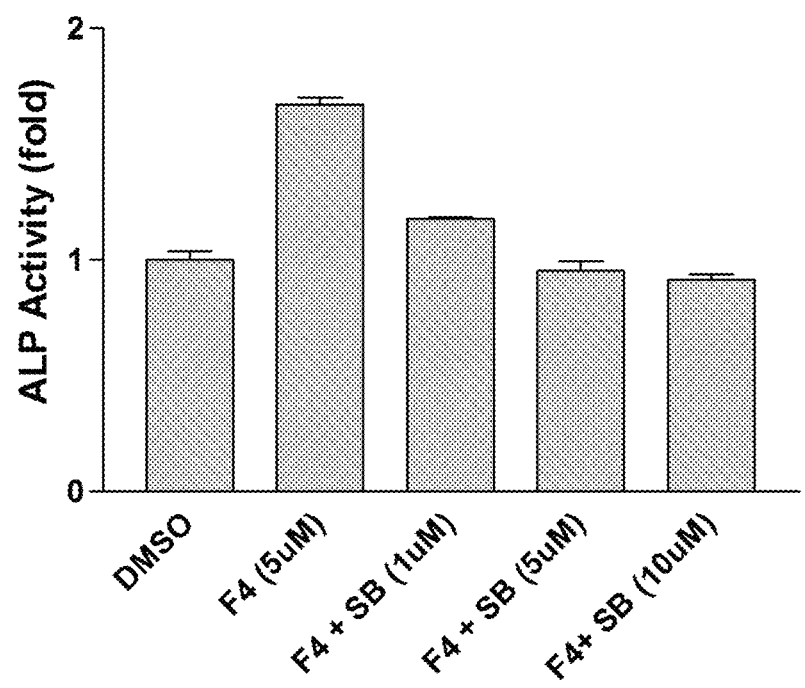

FIG. 3 is a bar graph showing the ALP activities in MC3T3-E1 osteoblasts treated with DMSO vehicle or 5 μM F4 in the presence or absence of p38 inhibitor SB203580 (SB) for a period of 2 days.

Figure 4:
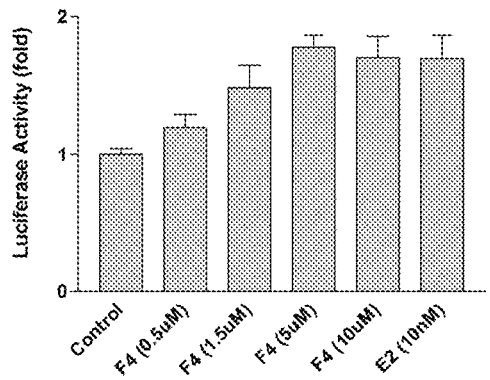
Figure 4:
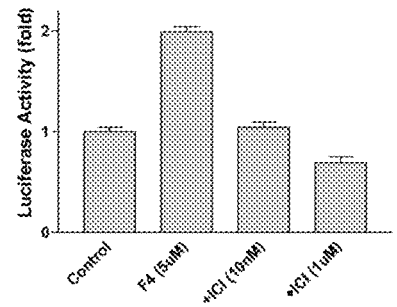
Figure 4:
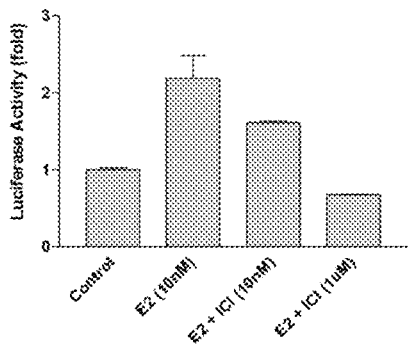
Figure 4:
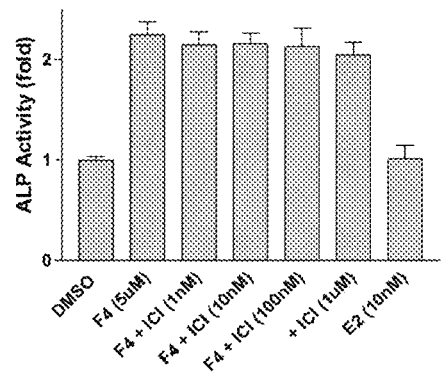
Figure 4:
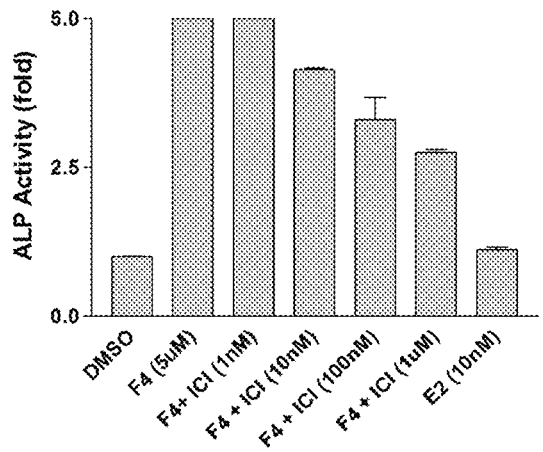

FIG. 4 is bar graphs showing (A) stimulation of ERE-mediated promoter activity by 0.5 μM, 1.5 μM, 5 μM, 10 μM of F4, or 10 nM estradiol (E2), in MC3T3-E1 osteoblasts; (B) inhibition of 5 μM F4-stimulated ERE promoter activity by ICI182780 at 10 nM and 1 μM concentrations; (C) inhibition of estradiol-stimulated ERE promoter activity by ICI182780 at 10 nM and 1 μM concentrations; effects of ICI182780 at 1 nM, 10 nM, 100 nM, 1 μM on ALP activity of MC3T3-E1 osteoblasts stimulated by 5 μM F4 at Day 4 (D) and Day 7 (E).

Figure 5:
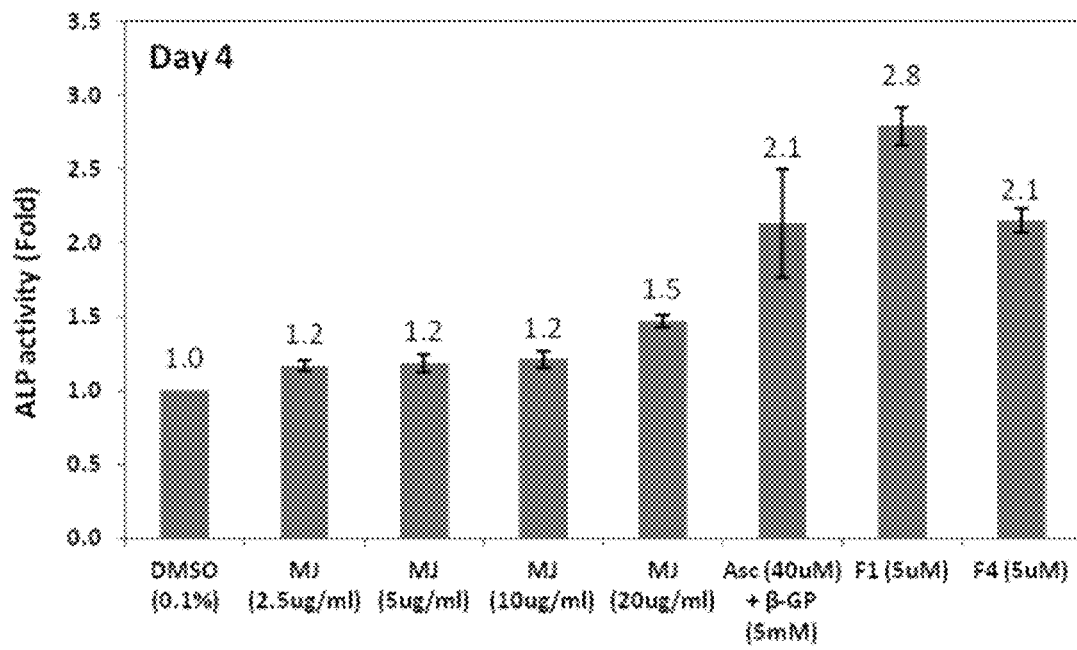
Figure 5:
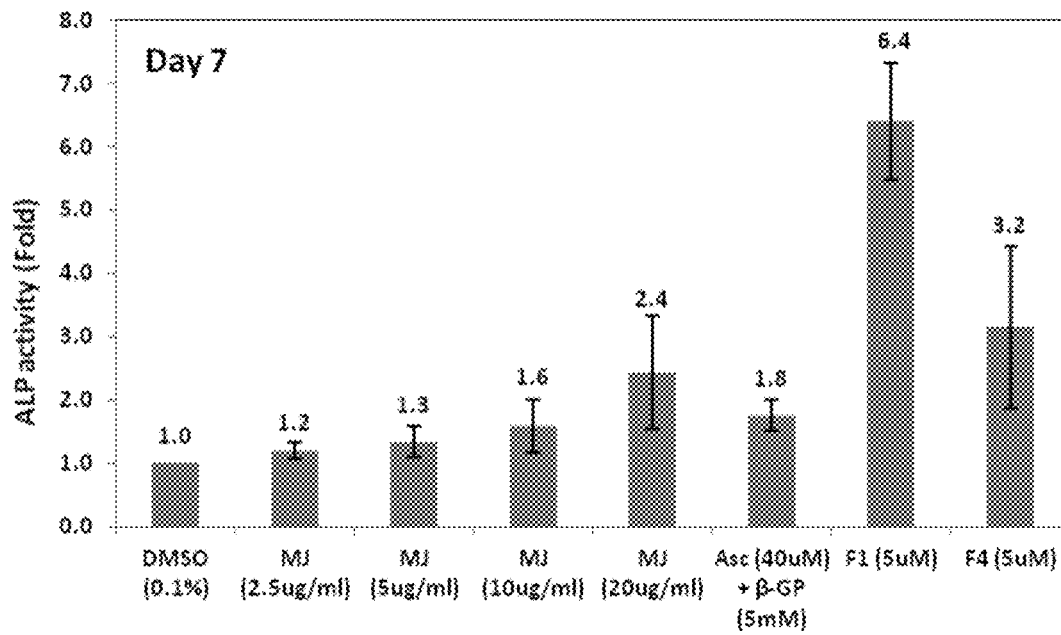

FIG. 5 is bar graphs showing effects on ALP enzyme activities of MC3T3-E1 osteoblasts when incubating with 0.1% DMSO, 2.5 μg/mL, 5 μg/mL, 10 μg/mL, 20 μg/mL Medulla Junci (MJ), 40 μM Ascorbate (Asc) plus 5 mM β-glycerophosphate (β-GP), 5 μM F1 or 5 μM F4 for a period of four days (A) and seven days (B).

Figure 6:
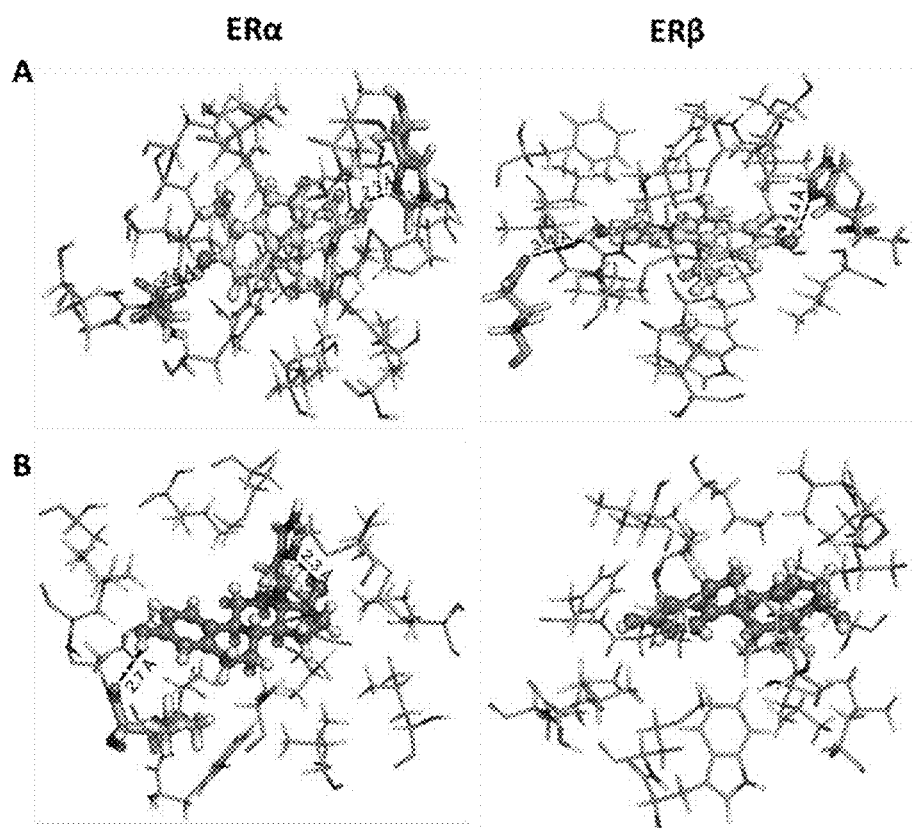

FIG. 6 shows models of effusol binding to estrogen receptors determined by Quantum Mechanics/Molecular Mechanics Calculation.

Figure 7:
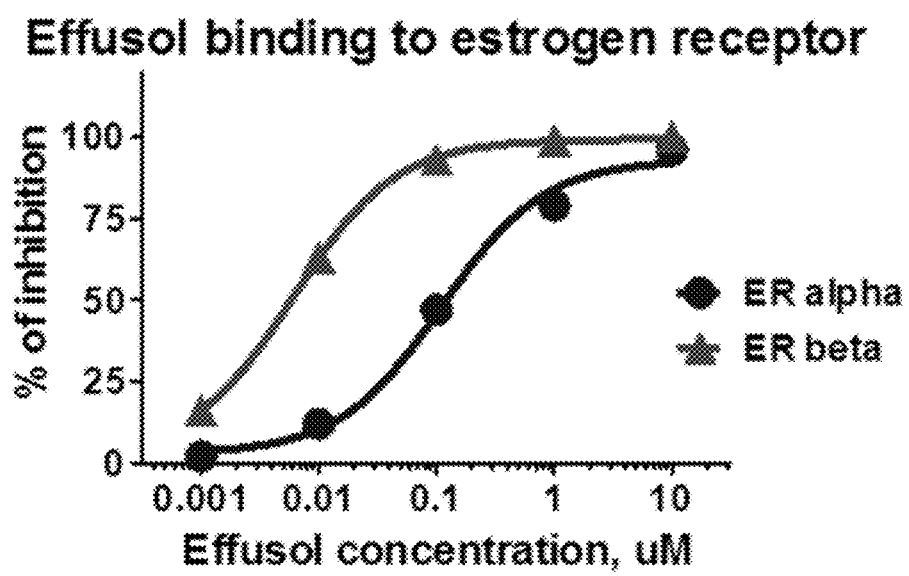

FIG. 7 is curves showing inhibition of radiolabeled 17beta-estradiol binding to estrogen receptor alpha and beta in the presence of indicated concentrations of F4.

Figure 8:
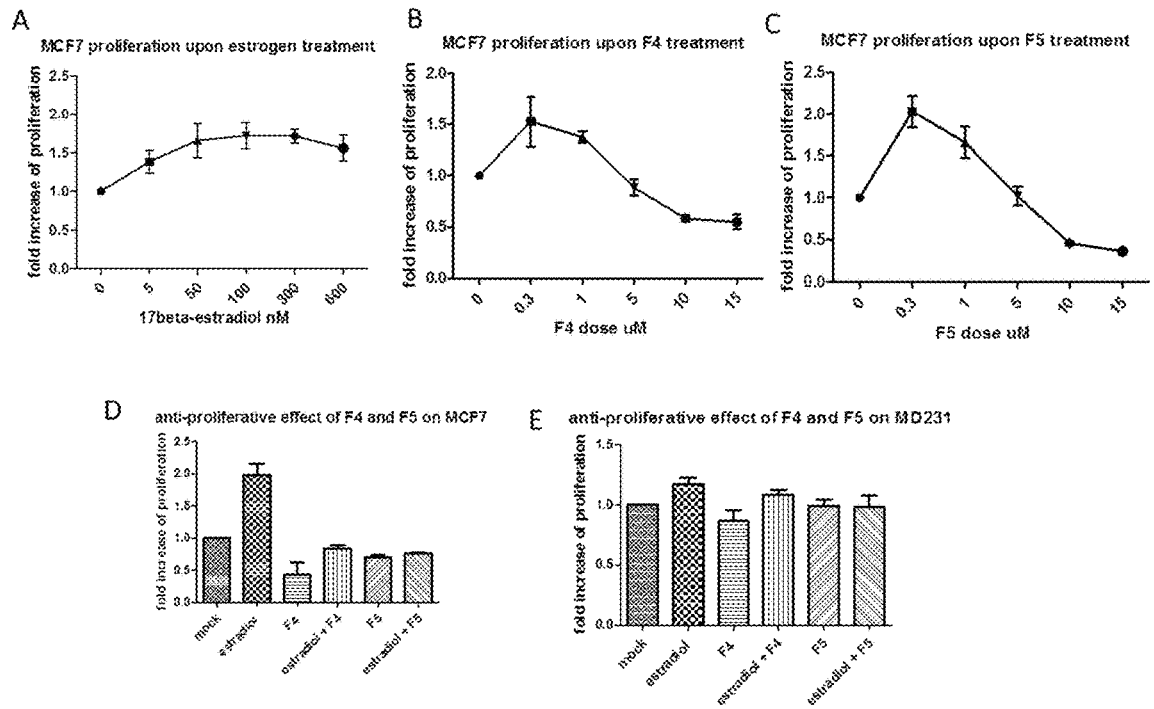

FIG. 8 is curves showing anti-proliferation property of F4 on estrogen treated breast cancer cells determined by bromodeoxyuridine (BrdU) incorporation assays. A shows fold increase in proliferation of MCF7 cells treated with 17beta-estradiol. B and C shows fold changes in proliferation of MCF7 cells treated with F4 and F5 at the indicated concentrations. D shows F4 (5 μM) and F5 (Dehydroeffusol, 5 μM) inhibited the cell proliferation induced by 17beta-estradiol in MCF7 cells (ER positive), but had no effect on MDA-MB-231 cells (ER negative) (E).

Figure 9:
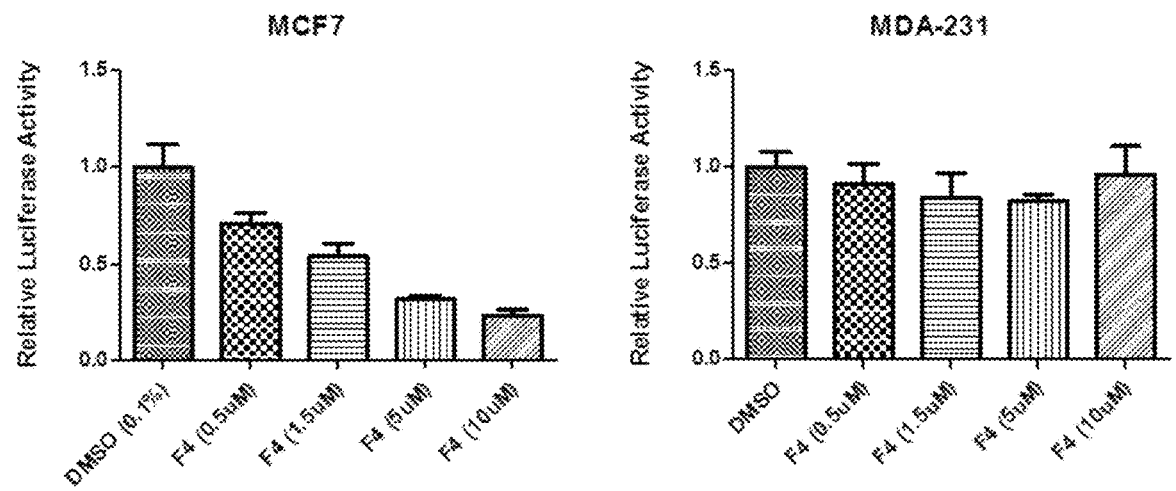

FIG. 9 is bar graphs showing luciferase activity of estrogen receptor responsive element reporter gene treatment upon F4. F4 treatment downregulates the estrogen receptor luciferase reporter activity of MCF7 cells (A), but not in MDA-MB-231 cells (B).

DETAILED DESCRIPTION OF THE INVENTION

The disclosed method and compositions may be understood more readily by reference to the following detailed description of particular embodiments and the Example included therein and to the Figures and their previous and following description.

Disclosed are compounds, compositions, and methods for treating or preventing bone loss or promoting bone formation in a subject in need thereof. In some forms, the method involves administering to the subject an effective amount of one or more phenanthrenes, or derivatives thereof, to reduce one or more symptoms of bone loss, prevent one or more symptoms of bone loss, promote bone formation, or combinations thereof, in the subject. In some forms, the reduction of one or more symptoms of bone loss, prevention of one or more symptoms of bone loss, promotion of bone formation, or combinations thereof, are relative to an untreated control.

In some forms, the composition is a pharmaceutical composition. In some forms, the pharmaceutical composition includes an active agent comprising one or more phenanthrenes, or derivatives thereof, in an amount effective to reduce one or more symptoms of bone loss, prevent one or more symptoms of bone loss, promote bone formation, or combinations thereof. In some forms, the reduction of one or more symptoms of bone loss, prevention of one or more symptoms of bone loss, promotion of bone formation, or combinations thereof, are relative to an untreated control.

In some forms, the one or more phenanthrenes comprise effusol. In some forms, the subject is human. In some forms, the subject has osteopenia or osteoporosis.

In some forms, the one or more phenanthrenes are administered or are present in the composition in an amount effective to stimulate osteoblast differentiation, activity, survival, or combinations thereof, in the subject. In some forms, the stimulation of osteoblast differentiation, activity, survival, or combinations thereof, is relative to an untreated control.

In some forms, the one or more phenanthrenes are administered or are present in the composition in an amount effective to enhance expression of one or more osteogenic proteins relative to an untreated control. In some forms, the one or more osteogenic proteins are selected from the group consisting of alkaline phosphatase, osteocalcin, osteoportin, osteonectin, bone sialoprotein, and combinations thereof.

In some forms, the one or more phenanthrenes are administered or are present in the composition in an amount effective to increase the levels of one or more osteoblast-specific transcription factors in the subject. In some forms, the increase in the levels of one or more osteoblast-specific transcription factors is relative to an untreated control. In some forms, the one or more osteoblast-specific transcription factors are selected from the group consisting of RUNX2, DLX5, SP7, and combinations thereof.

In some forms, the one or more phenanthrenes are administered or are present in the composition in an amount effective to increase phosphorylation of one or more mitogen-activated kinases (MAPKs) involved in osteoblast differentiation in the subject. In some forms, the increase in phosphorylation of one or more MAPKs involved in osteoblast differentiation is relative to an untreated control. In some forms, the one or more MAPKs is p38.

In some forms, the one or more phenanthrenes are administered in an amount effective to increase protein expression, transcript level, activity, or combinations thereof, of one or more members of the Wnt/β-catenin signaling pathway in the subject.

In some forms, the increase in protein expression, transcript level, activity, or combinations thereof, of one or more members of the Wnt/β-catenin signaling pathway is relative to an untreated control.

In some forms, the one or more phenanthrenes comprise effusol. In some forms, the one or more phenanthrenes consist essentially of effusol. In some forms, the one or more phenanthrenes consist of effusol.

In some forms, the effusol is enriched, purified, or combinations thereof, from *Juncus*. In some forms, the effusol is enriched, purified, or combinations thereof, from *Juncus effusus*. In some forms, the effusol is 10-fold, 20-fold, 30-fold, 40-fold, 50-fold, 60-fold, 70-fold, 80-fold, 90-fold, 100-fold, or more than 100-fold more concentrated than its concentration in crude extract from *Juncus*. In some forms, the effusol is 10-fold, 20-fold, 30-fold, 40-fold, 50-fold, 60-fold, 70-fold, 80-fold, 90-fold, 100-fold, or more than 100-fold more concentrated than its concentration in crude extract from *Juncus effusus*.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A. Definitions

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "subject" or "individual" refers to animals, especially mammals. For example, a subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. Preferred subjects are those in need of treatment with the disclosed compounds, compositions or methods.

The term "derivative," as relates to compounds, refers to a modified form of a compound (such as the disclosed compounds) having a chemical alterations. Such alterations, which can be referred to as modifications, can include, for example, hydrolysis, reduction, or oxidation products, of the compounds. Hydrolysis, reduction, and oxidation reactions are known in the art.

The term "functional derivative," as relates to compounds, refers to a derivative of a compound that retains a function of the compound, at least in part. For example, in the case of effusol, a functional derivative of effusol, in the context of the present disclosure, can include a derivative of effusol that retains, for example, the effect of stimulating osteoblast differentiation and activity in a subject with low bone mass such as osteopenia or osteoporosis.

The term "carrier" or "excipient" refers to an organic or inorganic, natural or synthetic inactive ingredient in a formulation, with which one or more active ingredients are combined. In some forms, a carrier or an excipient can be an inert substance added to a pharmaceutical composition to further facilitate administration of a compound, and/or does not cause significant irritation to an organism and does not abrogate the biological activity and properties of the administered compound. Carriers can be composed of, for example, materials that are considered safe and effective and may be administered to an individual without causing undesirable biological side effects or unwanted interactions. A carrier can be, for example, any components present in the pharmaceutical formulation other than the active ingredient or ingredients. The term "carrier" includes but is not limited to diluents, binders, lubricants, desintegrators, fillers, and coating compositions.

A carrier can also be a component of a coating composition, which can include plasticizers, pigments, colorants, stabilizing agents, and glidants. A delayed release dosage formulation can be prepared as described in references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995), which provide information on carriers, materials, equipment and process for preparing tablets and capsules and delayed release dosage forms of tablets, capsules, and granules.

The term "effective amount," as relates to a compound or compositions, refers to a nontoxic but sufficient amount of the compound to provide a desired or referenced result. The term "therapeutically effective amount" of a compound refers to a nontoxic but sufficient amount of the compound to provide a desired or referenced therapeutic result. For example, an effective amount can refer to a dosage sufficient to reduce, or inhibit a disorder, disease, or condition being treated, or to otherwise provide a desired pharmacologic and/or physiologic effect. The precise dosage will vary according to a variety of factors such as subject-dependent variables (e.g., age, immune system health, etc.), the severity of the disease or disorder being treated, as well as the route of administration and the pharmacokinetics of the agent being administered. As discussed elsewhere herein, and as is known, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need a disclosed composition for the treatment of diseases and conditions involving bone loss or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

The term "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. The term "pharmaceutically acceptable carrier" refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The terms "prevent," "prevention," and "preventing" means to administer a composition to a subject or a system at risk for or having a predisposition for one or more symptoms (e.g., bone loss) caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder. Preferably treatment for prevention would be prior to the onset of clinical symptoms of a disease or conditions so as to prevent a physical manifestation of aberrations associated with the disease or condition.

The term "inhibit," "suppress," "decrease," "interfere," and/or "reduce" (and like terms) generally refers to the act of reducing, either directly or indirectly, a function, activity, level, concentration, behavior, etc., relative to the natural, expected, or average or relative to current conditions. It is understood that this is typically in relation to some standard or expected value, in other words it is relative, but that it is not always necessary for the standard or relative value to be referred to. For example, something that inhibits, suppresses, decreases or reduces or interferes with bone loss might stop or slow the osteoblast apoptosis, or osteoclast activities. This can be a complete inhibition, suppression, decrease, interference, and/or reduction of the function, activity, level, concentration, behavior, etc. Inhibition, suppression, decrease, interference, and/or reduction can be compared to a control or to a standard level. Inhibition, suppression, decrease, interference, and/or reduction can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "increase," "enhance," "stimulate," "promote," and/or "induce" (and like terms) generally refers to the act of improving or increasing, either directly or indirectly, a function, activity, level, concentration, behavior, etc., relative to the natural, expected, or average or relative to current conditions. It is understood that this is typically in relation to some standard or expected value, in other words it is relative, but that it is not always necessary for the standard or relative value to be referred to. For example, something that increases, stimulates, promotes, induces or enhances bone formation might induce the production, and/or secretion of osteogenic molecules such as alkaline phosphatase, osteocalcin, osteoportin, osteonectin, bone sialoprotein, and collagen 1A1, in the context of osteoblast differentiation. Increase, enhancement, stimulation, promotion, and/or induction can be compared to a control or to a standard level. Increase, enhancement, stimulation, promotion, and/or induction can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140 145, 150, 155, 160, 165, 170, 175, 180, 185, 190, 195, 200, 210, 220, 230, 240, 250, 260, 270, 280, 290, 300, 320, 325, 340, 350, 360, 375, 380, 400, 425, 450, 475, 500, 550, 600, 650, 700, 750, 800, 850, 900, $10^3$, $10^4$, $10^5$, $10^6$, or $10^7$%.

The terms "treatment" and "treating" mean the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitiative terms. Thus, for example, characteristics or features of a disease, pathological condition, or disorder and/or symptoms of a disease, pathological condition, or disorder can be reduced to any effect or to any amount.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but include the knowledge that the subject is ill, or will be ill, as the result of a condition that is treatable by the compounds of the invention. For the disclosed treatment, subjects exhibiting or at risk for bone loss are preferred subjects in need or treatment.

The terms "administration," "administrating," and "administer" refer to contacting a substance, material, or product to the body of a subject. For example, administering a substance, material, or a product includes contacting the skin of a subject and injecting or implanting a substance, material, or product into the subject.

The term "parenteral administration" means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

The term "topical administration" means the non-invasive administration to the skin, orifices, or mucosa. Topical administrations can be administered locally, i.e., they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

The terms "bioactive agent" and "active agent," used interchangeably, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective," used interchangeably, refer to an amount (e.g. mass, volume, dosage, concentration, and/or time period) needed to achieve one or more desired result(s).

The term "biocompatible" refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "molecular weight" generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "consisting essentially of" limits the referenced material or subject matter to the specified materials or steps "and [to] those that do not materially affect the basic and novel characteristic(s)" of the referenced material or subject matter. *In re Herz,* 537 F.2d 549, 551-52 (CCPA 1976).

The term "bone loss" refers to a decrease in bone density, bone mass, or other measure of bone content. The term "symptom of bone loss" refers to effects that result from bone loss. Examples of symptoms of bone loss include bone fracture, receding gums, decreased grip strength, weak and brittle fingernails, cramps, muscle aches, bone pain, height loss, and low overall fitness. Symptoms of bone loss can also include physiological and metabolic measures related to bone formation and bone loss, such as measures of low bone density.

The term "bone formation" refers to formation of bone during growth and to addition to or increase in density of bone during bone remodeling. Bone remodeling is an ongoing turnover of bone in a process of resorption followed by replacement of bone with little change in shape. This is accomplished through osteoblasts and osteoclasts. The disclosed compounds, compositions, and methods are preferably are preferably used to increase or stimulate bone formation in the context of bone remodeling.

The terms "relative" and "relative to" refer to a condition, measure, level, etc., that is described in terms of a reference, control, or comparator condition, measure, level, etc.

The terms "involved" and "involved in," in the context of a biological process, refer to a biological process that is caused by or that affects a referenced product, condition, or process. For example, osteoblasts and osteoclasts are involved in bone remodeling.

The term "untreated control" refers to a subject generally similar to a treated subject (e.g., having the same disease or condition) that is treated with a control compound, composition, or method. A control compound, composition, or method is a compound, composition, or method that is the same as a treatment compound, composition, or method except for the absence or substitution of a specified component (e.g., the active ingredient).

The term "expression," in the context of genes and gene products, refers to the process by which information from a gene is used in the synthesis of a functional gene product. Expression can be measure in a variety of ways, including, for example, by measuring the level of one or more of the products of expression of the gene.

The term "osteopenia" refers to a condition in which bone mineral density is lower than normal, generally a bone mineral density T-score between −1.0 and −2.5. Osteopenia can be a precursor to osteoporosis. The term "osteoporosis" refers to a disease where decreased bone strength increases the risk of a broken bone. The underlying mechanism in all cases of osteoporosis is an imbalance between bone resorption and bone formation. The three main mechanisms by which osteoporosis develops are an inadequate peak bone mass (the skeleton develops insufficient mass and strength during growth), excessive bone resorption, and inadequate formation of new bone during remodeling. An interplay of these three mechanisms underlies the development of fragile bone tissue.

The term "osteoclast" refers to a type of bone cell that breaks down bone tissue. This function is critical in the maintenance, repair, and remodeling of bones of the vertebral skeleton. The osteoclast disassembles and digests the composite of hydrated protein and mineral at a molecular level by secreting acid and a collagenase, a process known as bone resorption. This process also helps regulate the level of blood calcium. The term "osteoclast differentiation" refers to the development of osteoclasts from precursor cells. It is generally understood that osteoclasts form by self-fusion of macrophages under the influence of activators. The term "osteoclast activity" refers to the breakdown of bone tissue by osteoclasts. The term can, as context indicates, refer to the overall process of bone breakdown or to any one or more component activities of the osteoclast as part of this process. The term "osteoclast survival" refers to the continued viability of osteoclasts. Generally, osteoclast function can be regulated or modulated in part by promotion or inhibition of osteoclast survival. For example, glucocorticoids can increase osteoclast survival.

The term "osteoblast" refers to a cell with a single nucleus that synthesizes bone. Osteoblasts are specialized, terminally differentiated products of mesenchymal stem cells. Osteoblasts synthesize dense, crosslinked collagen and specialized proteins in much smaller quantities, including osteocalcin and osteopontin, which compose the organic matrix of bone. The term "osteoblast-specific transcription factors" refers to transcription factors that are specifically repressed in osteoblasts. Preferred osteoblast-specific transcription factors are those that are involved in the bone formation activity of osteoblasts. Examples of osteoblast-specific transcription factors include RUNX2, DLX5, and SP7.

The term "osteogenic protein" refers to a protein that promotes bone formation and/or that guides bone tissue architecture.

The term "protein level" refers to the level (e.g., amount, concentration) of the referenced protein(s). The term "transcript level" refers to the level (e.g., amount, concentration) of the referenced transcript(s).

The terms "pathway" and "signaling pathway" refer to a group of molecules in a cell that work together to control one or more cell functions, such as cell division or cell death. After the first molecule in a pathway receives a signal, it activates another molecule. This process is repeated until the last molecule is activated and the cell function is carried out. Abnormal activation of signaling pathways can lead to cancer, and drugs are being developed to block these pathways. These drugs may help block cancer cell growth and kill cancer cells. The term "protein level," in the context of a signaling pathway, refers to the level of one or more proteins that are part of the signaling pathway. The term "transcript level," in the context of a signaling pathway, refers to the level of transcripts of one or more genes that encode proteins or regulatory elements that are part of the signaling pathway. The term "activity," in the context of a signaling pathway, refers to the level of activation of the signaling pathway.

As used herein, the term "phenanthrenes" refers to one of a group of polycyclic aromatic hydrocarbons composed of three fused six membered rings with two or three of the rings being aromatic.

The term "crude extract" refers to a partially purified or separated collection of material from a complex source, such as cells, tissue, or an organism. A crude extract generally refers to the product after a first step or first procedure breaking down or separating components from a complex source. Generally, a crude extract will include a significant amount of at least 25, 50, 75, 100, or 200 components.

The term "enriched," in the context of a compound or product, refers to a sample or preparation of or containing the referenced compound or product in which the concentration, relative abundance, or both, of the compound or product is increased relative to a prior, starting, or reference sample or preparation. A crude extract is an example of a prior, starting, or reference sample. The compound or product can be enriched to any suitable level. For example, the concentration, relative abundance, or both, of the compound or product can be increased by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140 145, 150, 155, 160, 165, 170, 175, 180, 185, 190, 195, 200, 210, 220, 230, 240, 250, 260, 270, 280, 290, 300, 320, 325, 340, 350, 360, 375, 380, 400, 425, 450, 475, 500, 550, 600, 650, 700, 750, 800, 850, 900, $10^3$, $10^4$, $10^5$, $10^6$, or $10^7$% relative to a prior, starting, or reference sample or preparation.

The term "purified," in the context of a compound or product, refers to a sample or preparation of or containing the referenced compound or product in which the concentration, relative abundance, or both, of the compound or product is increased relative to a prior, starting, or reference sample or preparation. The compound or product can be purified to any suitable level. For example, the concentration, relative abundance, or both, of the compound or product can be increased by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140 145, 150, 155, 160, 165, 170, 175, 180, 185, 190, 195, 200, 210, 220, 230, 240, 250, 260, 270, 280, 290, 300, 320, 325, 340, 350, 360, 375, 380, 400, 425, 450, 475, 500, 550, 600, 650, 700, 750, 800, 850, 900, $10^3$, $10^4$, $10^5$, $10^6$, or $10^7$% relative to a prior, starting, or reference sample or preparation.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist."

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and discussed and a number of modifications that can be made to a number of molecules including the compound are discussed, each and every combination and permutation and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Compounds

The compositions include one or more osteogenic compounds, or functional derivatives thereof. Generally, the one or more osteogenic compounds include one or more phenanthrenes, or derivatives thereof. Generally chemical structures of these phenanthrenes are shown in Formulas I, and II.

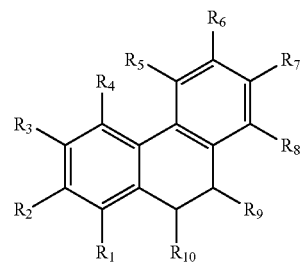

General chemical structures of phenanthrenes

Formula I

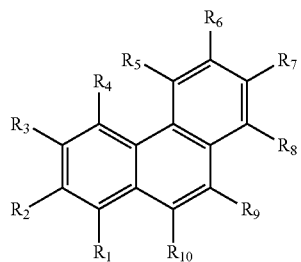

General chemical structures of phenanthrenes

Formula II

In Formula I and II, $R_1$, $R_2$, $R_3$, $R_4$, $R_5$, $R_6$, $R_7$, $R_8$, $R_9$ and $R_{10}$ are each independently H, akyl, alkenyl, alkynyl, halo, OH, O-acyl, O-akyl, O-alkenyl, O-monosaccharide, O-disaccharide, O-oligosaccharide, COR, COOR, CRR'OR", OSO$_3$H, OSO$_3$Na, N$_3$, NRR', NHSO$_2$R, SR, SOR, SO$_2$R, OPO$_3$H$_2$, OPO$_3$HNa, or OPO$_3$Na$_2$, and where R, R' and R" are each independently H, akyl, alkenyl, alkynyl. In some embodiments, $R_2$ is OH, R1 is methyl, $R_5$ is —CH=CH$_2$, $R_3$, $R_4$, $R_9$ and $R_{10}$ are H, and $R_6$, $R_7$, $R_8$ are each independently H, OH or CH$_3$.

In some embodiments, phenanthrenes such as F1, F4 (effusol), and derivatives thereof are included. Chemical structures of F1 and F4 are shown in Formulas III and IV.

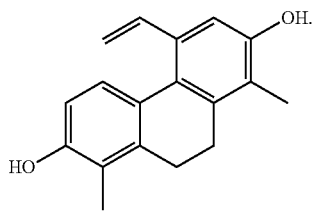

Chemical structure of F1

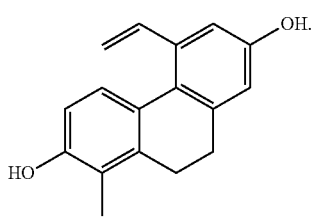

Chemical structure of F4 (Effusol)

In some embodiments, the one or more osteogenic compounds include one or more phenanthrenes that carry out similar function as phytoestrogen. For example, one or more phenanthrenes are osteogenic at least in part due to their binding towards estrogen receptors.

In some embodiments, the compositions are derived from natural products from Chinese medicines. One embodiment provides purified phenanthrenes from a common and inexpensive Chinese medicinal material Medulla Junci.

In further embodiments, the compositions include effusol purified and enriched from Medulla Junci. Thus, effusol is enriched 2-fold, 5-fold, 10-fold, 20-fold, 30-fold, 40-fold, 50-fold, 60-fold, 70-fold, 80-fold, 90-fold, 100-fold, or more than 100-fold more concentrated than its concentration in crude extract from any natural products such as Medulla Junci. In some embodiments, the composition including effusol is not crude extract of any natural plants such as Medulla Junci. In yet further embodiments, the compositions including effusol is chemically synthesized, thus not derived from any natural products.

In some embodiments, the compositions exhibit effective osteogenic activity. In preferred embodiments, the compositions exhibit effective osteogenic activity through, at least in part, its phytoestrogenic property.

In one aspect described herein are compounds having the structure of Formula I, II, III, or IV or a pharmaceutically acceptable salt or ester thereof. Formula I, II, III, and IV also encompass pharmaceutically acceptable salts. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of the compounds to the base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as defined above but is not obtained, enriched, or purified from a plant, such as a *Juncus* plant. As another example, as one option, a group of compounds is contemplated where each compound is as defined above but is not obtained, enriched, or purified from a medicinal extract, such as a Medulla Junci. As another example, a group of compounds is contemplated where each compound is as defined above and is able to prevent or reduce bone loss. F1 and F4 can be independently and specifically included or excluded from the compounds and methods disclosed herein.

B. Compositions

Compositions including an effective amount of one or more natural phenanthrenes for treating, or preventing bone loss are disclosed. Typically, administration of the composition is effective to reduce or inhibit bone resorption, and/or increase bone formation in a subject in need thereof.

One embodiment provides compositions that are effective in stimulating osteoblast differentiation, osteoblast activities, and/or reduce osteoblast apoptosis, at/near the site of treatment. In some embodiments, the composition enhances the rate of calcium deposition by osteoblasts into bone matrix.

A further embodiment provides compositions that are effective in reducing, or inhibiting bone resorption by osteoclasts at/near the site of treatment.

In some embodiments, the disclosed compositions cause direct or indirect induction of protein, transcript, and/or activity of osteoblast-specific secreted proteins. Exemplary osteoblast-specific secreted proteins include alkaline phosphatase, osteocalcin, osteoportin, osteonectin, bone sialoprotein, and collagen 1A1.

Still another embodiment provides compositions that cause direct or indirect induction of osteoblast-specific genes include transcription factors such as RUNX2, DLX5 and SP7 (Osterix). In some embodiment, the compositions increase levels of phosphorylation of one or more osteoblast-specific genes include transcription factors such as RUNX2, DLX5 and SP7 (Osterix).

Yet another embodiment provides compositions that cause direct or indirect osteoblastogenesis via activation in the Wnt/β-catenin signaling pathway. Activation of Wnt/β-catenin signaling occurs upon binding of Wnt to the 7-transmembrane domain-spanning frizzled receptor and low-density lipoprotein receptor-related protein 5 and 6 (LRP5/6) co-receptors (Krishnan V et al., *J Clin Invest.* 116(5): 1202-1209 (2006)). Signals are generated through the proteins Disheveled, Axin, and Frat-1, which disrupt the protein complex and inhibit the activity of GSK3, thus causing hypophosphorylation of its substrate, β-catenin. Stabilized β-catenin then accumulates in the cytosol and translocates to the nucleus, where this transcriptional coactivator interacts with T cell factor/lymphoid enhancer binding factor (TCF/LEF) transcription factors to mediate many of the effects of Wnts on gene transcription.

Thus, in some embodiments, the disclose compositions cause direct or indirect activation, and/or protein levels of β-catenin, and any downstream gene transcription regulated by β-catenin. In other embodiments, the disclose compositions cause direct or indirect increase in protein expression, transcript level, and/or activity of one or more members of the Wnt/β-catenin signaling pathway. For example, an increase in the transcript levels of Wnt3A, Wnt receptor frizzled 1, β-catenin, and combinations thereof.

On study showed that BMP2-induced osteoblast differentiation mediates mild ER stress-activated ATF6 and directly regulates osteocalcin expression (Jang W G et al., *J Biol Chem.* 287, 905-15 (2012)). Thus, a further embodiment provides compositions that cause direct or indirect increase in endoplasmic reticulum (ER) stress. In some embodiments, the disclosed compositions cause direct or indirect increase in expression, transcription, and/or activity of ATF6.

Another embodiment provides compositions that cause direct or indirect increase in the activities of one or more mitogen-activated kinases (MAPKs) involved in the osteoblast differentiation. Exemplary MAP kinases include extracellular signal-regulated kinases 1/2 (ERK1/2), ERK5, c-Jun amino (N)-terminal kinases 1/2/3 (JNK1/2/3), and the p38 isoforms (p38α, p38β, p38γ, and p38δ). In some embodiments, the disclose compositions cause increase in the level of phosphorylation of one or more mitogen-activated kinases (MAPKs) involved in the osteoblast differentiation. One specific embodiment provides compositions that cause direct or indirect increase in the total phosphorylated p38.

In some embodiment, the compositions cause direct or indirect increase in phosphorylation of one or more downstream molecules of the mitogen-activated kinases (MAPKs) including p38. Exemplary molecules include Runx2, Dlx5, Osx, and ATF4.

In some embodiment, the compositions increase osteoblast differentiation, and/or activity, at least in a part through estrogen receptors. In some embodiment, the compositions exert effect similar to phytoestrogen such as estradiol. In some embodiment, the compositions have phytoestrogen-like properties. Thus in some embodiments, the compositions are suitable for treatment of menopausal symptoms and other diseases in which phytoestrogenic activities are required.

C. Additional Therapeutic, Prophylactic or Diagnostic Agents

The disclosed compositions can be administered in combination or alternation with one or more additional therapeutic, diagnostic, and/or prophylactic agents. For example, one or more additional therapeutic, diagnostic, and/or prophylactic agents can reduce, or inhibit bone loss.

The amount of a second therapeutic generally depends on the severity of the condition to be treated. Specific dosages can be readily determined by those of skill in the art. See Ansel, Howard C. et al. *Pharmaceutical Dosage Forms and Drug Delivery Systems* (6$^{th}$ ed.) Williams and Wilkins, Malvern, PA (1995).

In some cases, one or more additional active agents may be dispersed in, or otherwise associated with particles in the formulation. In certain embodiments, one or more additional active agents may also be dissolved or suspended in the pharmaceutically acceptable carrier.

In some cases, the active agent is a diagnostic agent imaging or otherwise assessing the inflammatory conditions. Exemplary diagnostic agents include paramagnetic molecules, fluorescent compounds, magnetic molecules, and radionuclides, x-ray imaging agents, and contrast media.

There are several medications that can slow or stop bone loss which helps reduce the risk of fractures. In addition, some of these medications can be used for patients diagnosed with osteopenia to prevent osteoporosis. Commonly used medications for the prevention and treatment of osteoporosis are bisphosphonates, selective estrogen receptor modulators (SERMS), calcitonins, and parathryoid hormones.

In some embodiments, the disclosed composition is used in combination with one or more bisphosphonates. Bisphosphonates inhibits the resorption of bone by osteoclasts which help maintain bone density. The different bisphosphonates used to treat osteoporosis are alendronate (FOSAMAX®), risedronate (ACTONEL®), ibandronate (BONIVA®), and zoledronic acid (RECLAST®).

In some embodiments, the disclosed composition is used in combination with one or more selective estrogen receptor modulators (SERMS). SERMS work as either estrogen antagonist or agonists depending on the tissue type. For bone tissue, SERMs act as estrogen agonists and increase bone density. Exemplary SERMs used to treat osteoporosis include raloxifene (EVISTA®).

In some embodiments, the disclosed composition is used in combination with one or more hormones, or hormone-like medications. Calcitonin is a hormone that is normally found in the body and is released by the thyroid. It is involved in calcium regulation and bone metabolism. Calcitonin lowers calcium levels in the blood by having the bones retain the calcium. The different calcitonins used to treat osteoporosis are FORTICAL®, and MIACALCIN®.

In some embodiments, the disclosed composition is used in combination with one or more parathyroid hormones. Parathyroid hormones are normally found in the human body and help regulate calcium and phosphate levels. They work by stimulating bone growth and decreasing bone loss. The only FDA approved parathyroid hormone is teriparatide (FORTEO®).

In some embodiments, the disclosed composition is used in combination with one or more antibodies that target osteoclasts. For example, the anti-RANKL (receptor activator of nuclear factor-κB ligand) antibody, denosumab (PROLIA®), reduces osteoclast differentiation and activity.

In some embodiments, the disclosed composition is used in combination with one or more dietary supplements. Exemplary supplements include calcium, magnesium, vitamins D, K, C, boron, copper, dehydroepiandrosterone (DHEA), eicosapentaenoic acid (EPA) and docosahexaenoic acid (DHA), Folic acid, vitamin B6, and vitamin B12, Manganese, Silicon, Strontium, and Zinc.

In some embodiments, one or more therapeutic, prophylactic or diagnostic agent is administered prior to, in conjunction with, subsequent to, or alternation with treatment using the disclosed compositions.

D. Formulations

Formulations and pharmaceutical compositions containing an effective amount of the composition in a pharmaceutical carrier appropriate for administration to a subject in need thereof to reduce or inhibit bone loss, and/or promote osteoblast differentiation and bone formation, are provided. The compositions designed to be administered locally or systemically.

Formulations are prepared using a pharmaceutically acceptable carrier. Carriers can be composed of materials that are considered safe and effective and may be administered to an individual without causing undesirable biological side effects or unwanted interactions. The term "carrier" can, for example, refer to all components present in the pharmaceutical formulation other than the active ingredient or ingredients. The term "carrier" includes but is not limited to diluents, binders, lubricants, desintegrators, fillers, and coating compositions.

A carrier can also be a component of a coating composition, which can include plasticizers, pigments, colorants, stabilizing agents, and glidants. A delayed release dosage formulation can be prepared as described in references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995), which provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, PA: Williams & Wilkins, 1995).

A preferred method for preparing extended release tablets is to compress a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

i. Excipients

In addition to a therapeutic or prophylactic agent (or possibly other desired molecules for delivery), the particles can include excipients such as a sugar, such as lactose, a protein, such as albumin, and/or a surfactant.

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

2. Enteral Administration

The compositions are generally formulated for oral delivery.

i. Additives for Oral Administration

Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present active compounds and derivatives. See, e.g., Remington's Pharmaceutical Sciences, 18th Ed. (1990, Mack Publishing Co., Easton, Pa. 18042) pages 1435-1712. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

ii. Chemically Modified Forms for Oral Dosage

The disclosed compositions can be chemically modified so that oral delivery of the derivative is efficacious. Generally, the chemical modification contemplated is the attachment of at least one moiety to the component molecule itself, where said moiety permits (a) inhibition of degradation; and (b) uptake into the blood stream from the stomach or intestine. Also desired is the increase in overall stability of the component or components and increase in circulation time in the body. PEGylation is a preferred chemical modification for pharmaceutical usage. Other moieties that can be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189).

3. Parenteral and Topical Administration

In some embodiments, the compositions are generally formulated for parenteral or topical administration.

i. Solutions, Gels, Ointments and Suspension

Numerous parenteral or topical formulations are known and available. Solutions can be the sterile filtered, concentrated or diluted with water, buffered saline, or an equivalent, formed into a gel with a polysaccharide such as alginate or hyaluronic acid, polyvinyl pyrrole, or ointment such as petrolatum or mineral oil, or emulsified with lipid or oil.

Emulsions are generally dispersions of oily droplets in an aqueous phase. There should be no evidence of breaking or coalescence.

Suspensions contain solid particles dispersed in a liquid vehicle; they must be homogeneous when shaken gently and remain sufficiently dispersed to enable the correct dose to be removed from the container. A sediment may occur, but this should disperse readily when the container is shaken, and the size of the dispersed particles should be controlled. For ophthalmic application, the active ingredient and any other suspended material must be reduced to a particle size small enough to prevent irritation and damage to the cornea.

Ointments are sterile, homogeneous, semi-solid preparations intended for application to the surface, such as the skin, the conjunctiva or the eyelids. They are usually prepared from non-aqueous bases, e.g., soft paraffin (Vaseline), liquid paraffin, and wool fat. They may contain suitable additives, such as antimicrobial agents, antioxidants, and stabilizing agents.

The composition can be formulated for parenteral delivery, such as injection or infusion, in the form of a solution or suspension, or a powder. The formulation can be administered via any route, such as, the blood stream or directly to the organ or tissue to be treated.

The composition can also be formulated for topical delivery (e.g., to a mucosal surface such as the mouth, conjunctiva, intranasal, intravaginally, etc.). The particles may be provided in a lyophilized or dried form in a unit dosage form, for suspension at the time of injection. These may be provided in a kit with an appropriate amount of diluent such as sterile water or buffered solution.

The formulations can be prepared as aqueous compositions using techniques known in the art. The compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the compounds or nanoparticles can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles.

The formulation is typically buffered to a pH of between 3 and 8 for parenteral or topical administration upon reconstitution. Suitable buffers include, but are not limited to, phosphate buffers, acetate buffers, and citrate buffers. Ideally, the pH of ophthalmic drops should be equivalent to that of tear fluid, which is 7.4. However, the decision to add a buffering agent should be based on stability considerations. The pH selected should be the optimum for both stability of the active pharmaceutical ingredient and physiological tolerance. If a buffer system is used, it must not cause precipitation or deterioration of the active ingredient. The influence on the lachrymal flow should also be taken into account.

Water soluble polymers are often used in formulations for parenteral or topical administration. Suitable water-soluble polymers include, but are not limited to, polyvinylpyrrolidone, dextran, carboxymethylcellulose, and polyethylene glycol.

Sterile injectable solutions can be prepared by incorporating the compound or nanoparticles in the required amount in the appropriate solvent or dispersion medium with one or more of the excipients listed above, as required, followed by filtered sterilization. Generally, dispersions are prepared by incorporating the various sterilized compositions into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the compound or nanoparticle plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral or topical administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, acceptable diluent or solvent such as 1,3-butanediol.

In some instances, the formulation is distributed or packaged in a liquid form. Alternatively, formulations for parenteral or topical administration can be packed as a solid, obtained, for example by lyophilization of a suitable liquid formulation. The solid can be reconstituted with an appropriate carrier or diluent prior to administration.

Solutions, suspensions, or emulsions for parenteral or topical administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral or topical administration may also contain one or more tonicity agents to adjust the isotonic range of the formulation. Suitable tonicity agents are well known in the art. Examples include glycerin, mannitol, sorbitol, sodium chloride, and other electrolytes.

Solutions, suspensions, or emulsions for parenteral or topical administration may also contain one or more preservatives to prevent bacterial contamination of the tropical preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

In some forms, the carrier can comprise a cream, paste, fluid, coating, paint, spray, detergent, or a combination thereof. In some embodiments, the disclosed compositions can be used in any forms that come to direct and/or indirect contact with the skin. For example, in body cream/paste/lotion/gel, body soap, skin wash, laundry detergent, skin spray, wound cleanser, wound covering, shampoo, shower gel, facial wash, facial cream, or facial soap.

In some embodiments, the compositions can further comprise a carrier that enhances the delivery of the compositions to the cells of interest, e.g., keratinocytes and macrophages associated with the pathogenesis of psoriasis. A carrier can be barrier-disrupting agent or a penetration-enhancing vehicle. Exemplary penetration-enhancing vehicles include a humectant (e.g., glycols, glycerols), powder, (e.g., clays, shake lotions), oil/water (O/W) emulsion (e.g., aqueous creams), water/oil emulsion (e.g., oily creams), emulsifying base (e.g., anhydrous lipid and O/W emulsifiers), absorption base (e.g., anhydrous lipid and W/O emulsifiers), lipophilic (e.g., fats, waxes, oils, silicones), salicylic acid, urea phospholipase A2, phosphatidylcholine dependent phospholipase C, ethanol, acetone, detergents, bases, propylene glycol, pyrriolidones, dimethylacetamide, dimethylformamide, dimethylsulfoxide, alkyl sulfoxide, phosphine oxide, surfactants and caprolactams such as azone, amines and amides, alkyl N,N-distributed-amino acetates, decylmethylsulfoxide, pyrrolidones, pirotiodecane (HPE-101), benzlyalkonium, benzylalkonium chloride polymers, silicone based polymers, fatty acids, cyclic ureas, terpenes, liposomes, cyclodextrins, and combinations thereof.

E. Kits

Medical kits are also disclosed. Typically, the described compositions are prepared using a pharmaceutically acceptable carrier composed of materials that are considered safe and effective and may be administered to an individual without causing undesirable biological side effects or unwanted interactions. A kit can include one or more of the compounds or compositions described. For example, a kit can be a container that includes a compound of effusol. A kit can further include one or more medications (e.g., bisphosphonates). A kit can be ready for administration. A kit can additionally include directions for use of the kit (e.g., instructions for treating a subject).

F. Mixtures

Disclosed are mixtures formed by performing or preparing to perform the disclosed method. For example, disclosed are mixtures comprising one or more of the disclosed compounds and a carrier.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

Methods

Disclosed are methods for treating or preventing bone loss or promoting bone formation in a subject in need thereof. In some forms, the method involves administering to the subject an effective amount of one or more phenanthrenes, or derivatives thereof, to reduce one or more symptoms of bone loss, prevent one or more symptoms of bone loss, promote bone formation, or combinations thereof, in the subject. In some forms, the reduction of one or more symptoms of bone loss, prevention of one or more symptoms of bone loss, promotion of bone formation, or combinations thereof, are relative to an untreated control.

A. Methods of Reducing Bone Loss

Methods of using the compositions to reduce or prevent bone loss in a subject are provided. Methods of using the compositions to promote osteoblast differentiation, and/or bone formation in a subject are also provided.

Methods typically include administering a subject in a need thereof an effective amount of a composition including one or more phenanthrenes such as effusol, or functional derivatives thereof. In preferred embodiments, the compositions include one or more phenanthrenes having phytoestrogen-like functions. In some embodiments, the subject is in need of treatment for osteopenia, or osteoporosis.

Methods of using the compositions to treat or prevent osteopenia are described. Methods of using the compositions to treat or prevent osteoporosis are also described. Methods of using the compositions to increase bone mass/density are also provided, preferably through osteoblast differentiation.

In some embodiments, the disclosed compositions are administered to a subject in an effective amount to reduce or inhibit bone resorption, and/or increase bone formation in a subject in need thereof. In some embodiments, the disclosed compositions are effective at reducing rate of bone resorption by 5%, 10%, 20%, 30%, 40%, 50%, 60%, 70%, 80%, 90%, 100%, 200%, or more than 200%. In some embodiments, the disclosed compositions increase the rate of calcium deposition by osteoblasts into bone matrix by 5%, 10%, 20%, 30%, 40%, 50%, 60%, 70%, 80%, 90%, 100%, 200%, or more than 200%.

Methods of using the compositions to increase one or more osteogenic molecules, through mRNA, and/or protein expression, are also provided. Exemplary osteogenic molecules include osteoblast-specific secreted proteins include alkaline phosphatase, osteocalcin, osteoportin, osteonectin, bone sialoprotein, and collagen 1A1. Exemplary osteogenic transcription factors include RUNX2, DLX5 and SP7 (Osterix). In some embodiments, the disclosed compositions increase one or more osteogenic molecules directly, and/or indirectly, by 5%, 10%, 20%, 30%, 40%, 50%, 60%, 70%, 80%, 90%, 100%, 200%, or more than 200%.

Methods of using the compositions to increase one or more members of the Wnt/β-catenin signaling pathway are described. Typically, the disclosed compositions are effective in increasing the activity and/or quantity of one or more members associated with the Wnt/β-catenin signaling pathway including Wnt3A, Wnt receptor frizzled 1, Disheveled, Axin, Frat-1, and/or β-catenin. In some embodiments, the disclosed compositions lead to direct, and/or indirect increase in the transcript level of one or more members of the Wnt/β-catenin signaling pathway by 5%, 10%, 20%, 30%, 40%, 50%, 60%, 70%, 80%, 90%, 100%, 200%, or more than 200%.

Methods of using the compositions to increase endoplasmic reticulum (ER) stress, and/or in expression, transcription, and/or activity of ATF6 are provided. Methods of using the compositions to increase activities of one or more mitogen-activated kinases (MAPKs) involved in the osteoblast differentiation are also provided. In some embodiments, the disclosed compositions lead to direct, and/or indirect increase in the total phosphorylated p38 by 5%, 10%, 20%, 30%, 40%, 50%, 60%, 70%, 80%, 90%, 100%, 200%, or more than 200%.

Methods of using the compositions to increase signaling through estrogen receptors are also described. In some embodiments, the disclosed compositions lead to direct, and/or indirect increase in signaling through estrogen receptor by 5%, 10%, 20%, 30%, 40%, 50%, 60%, 70%, 80%, 90%, 100%, 200%, or more than 200%, measured by any of its downstream effector molecules.

A. Administration

Pharmaceutical compositions for reducing loss of bone mass can be administered in a number of ways depending on the severity of conditions to be treated. The methods for administering the disclosed compositions are essentially the same, whether for prevention or treatment.

In some embodiments, the disclosed compositions are included in food products, or nutritional products such as dietary supplement. In some embodiments, the disclosed compositions are included in products such as tea, coffee, soda drinks, energy drink, breakfast cereal and snack bars.

The composition can be administered during a period before, during, or after onset of disease symptoms, or any combination of periods before, during or after onset of one or more disease symptoms. For example, the subject can be administered one or more doses of the composition every 1, 2, 3, 4, 5, 6, 7, 14, 21, 28, 35, or 48 days prior to onset of disease symptoms. The subject can be administered one or more doses of the composition every 1, 2, 3, 4, 5, 6, 7, 14, 21, 28, 35, or 48 days after the onset of disease symptoms. In some embodiments, the multiple doses of the compositions are administered before an improvement in disease condition is evident. For example, in some embodiments, the subject receives 1, 2, 3, 4, 5, 6, 7, 14, 21, 28, 35, or 48, over a period of 1, 2, 3, 4, 5, 6 7, 14, 21, 28, 35, or 48 days or weeks before an improvement in the disease condition is evident.

The compositions can be administered alone, or in combination with a second active agent, as part of therapeutic regime for disease treatment. For example, the composition can be administered on the first, second, third, or fourth day, or combinations thereof. The composition can be administered on the same day, or a different day than the second active agent.

Any of the compounds can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The compounds and pharmaceutical compositions described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

B. Conditions to be Treated

The disclosed compositions are particularly suited to treat conditions involving low bone mass in a subject. For example, the disclosed methods can be used to prophylactically or therapeutically inhibit, reduce, alleviate, or permanently reverse bone loss.

In some embodiments, the subject has osteopenia. In other embodiments, the subject has osteoporosis. In further embodiments, the subject is in a high-risk group for developing osteoporosis. High-risk groups include women after menopause, those with family history of low bone mass, men and women above the age of 50, those with other medical conditions such as hyperthyroidism, hyperparathyroidism, and/or Cushing's syndrome, that contribute to bone loss, and those with a poor diet with a lack of calcium and vitamin D, smoking, excessive use of alcohol or caffeine, and lack of exercise.

Bone mineral density (BMD) is the measurement of calcium levels in bones, which can estimate the risk of bone fractures. It is also used to determine if a patient has osteopenia or osteoporosis. Bone mineral density tests are noninvasive and painless procedures usually done on the hip, spine, wrist, finger, shin bone, or heel.

While osteopenia may be diagnosed using plain radiographs, the most common method for measuring BMD (and a way to definitively diagnose osteoporosis) is through Dual Energy X-ray Absorptiometry or DEXA. This scan uses low-energy x-rays that expose patients to much less radiation than standard x-rays and can assess calcium levels in bone. The results are measured as a "score" and are compared to those of healthy individuals.

A patient's BMD is given a T-score, which is derived by comparing it to an average score for a healthy 30-year-old of the same sex and race. The difference between the "norm al young" score and the patient's score is referred to as a standard deviation (SD). T-scores ranging from 2.5 to −1 SD are considered normal bone density. Patients with T-scores between −1 SD and −2.5 SD are diagnosed with osteopenia and are considered at high risk for osteoporosis. Patients with T-scores lower than −2.5 SD are diagnosed with osteoporosis.

The formulations may be administered to animals as well as to humans to prevent, or treat any disorders associated with low bone mass. Preferred animals include dogs, cats, horses, as well as other animals that can be treated including livestock (cattle, sheep, swine, goats). The compositions and methods are useful for managing or treating joint disorders in horses. The formulation can be administered prophylactically or therapeutically. In many cases, regular administration is used to prevent further damage. Examples of horses requiring prophylactic treatment include racehorses, barrel, reining, and cutting horses, jumpers and dressage horses.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder and the treatment being effected, the number of times daily and number of days or weeks of treatment, and whether the probiotics are administered concurrently with antibiotics.

The selected dosage depends upon the desired therapeutic effect, on the route of administration, and on the duration of the treatment desired. Preferably, the amount of the composition administered is effective to prevent or reduce bone loss in a subject compared to an untreated control.

In some embodiments, the dosage is about 0.1-100 mg for every kilogram of weight of the subject under treatment. Preferably, it is about 1-20 mg/kg.

C. Controls

The effect of the described composition can be compared to a control. Suitable controls are known in the art and include, for example, an untreated subject, or a placebo-treated subject. In some embodiments, an untreated control subject suffers from, the same disease or condition as the treated subject e.g., osteoporosis, preferably having a similar degree of severity. In some embodiments, a suitable control is an area having the same bone density as the area being treated on the same subject. For example, a patient with osteoporosis on both wrists can treat one wrist locally with the compositions, whilst use the other as a control.

The present invention will be further understood by reference to the following non-limiting examples.

EXAMPLES

Example 1: F Compounds Induced Cell Differentiation and Mineralization of MC3T3-E1 Osteoblasts 1. Methods and Materials Cell Culture MC3T3-E1 (passage 4-10) was maintained in Minimal Essential Media (MEM) supplemented with 10% FBS, 1 mM Sodium Pyruvate and 1% 100 ug/ml penicillin-streptomycin (100 U/ml). All reagents are from GIBCO Life Technologies.

Cell Viability Assays

MC3T3-E1 cells were seeded at 7×103 cells/well in 96-well plates for 2 days. Cells were treated with serial dilution of F4 (highest conc. at 10 µM). After treatment, cells were fixed with 3% formalin and stained with NBB solution (0.05% NBB with 0.1 M sodium acetate and 9% acetic acid) at room temperature. Twenty four hours later, staining solution was removed and distilled water was added to remove free dye. Then, 100 ul of 50 mM NaCl was added to dissolve bound dye and recorded absorbance at 590 nm.

Alkaline Phosphatase (ALP) Assays

MC3T3-E1 cells were seeded at 1×105 cells per well in 24-well plate. Twenty four hours later, cells were treated with F4 at 0.5 µM, 1.5 µM, 5 µM and 0.1% DMSO (vehicle control) and ascorbic acid (ASC, 400 µM)/β-glycophosphate (β-GP, 5 mM) as positive control. After treatment, cells were washed twice with PBS and lysed with buffer contains 50 mM Tris pH7.4 and 0.1% Triton X-100. After 3 freeze-thaw cycles, 40 ul of cell lysate was mixed with 50 ul of 2× Assay buffer (2-Amino-2methyl-1-propanol, pH 10.4 with 4 mM $MgCl_2$) and 10 ul of 0.1M 4-Nitrophenyl phosphate. Incubated in 37° C. and recorded at OD410.

Osteoblast Mineralization Assays

MC3T3-E1 cells were seeded at 1×105 cells per well in 24-well plates. Cells were cultured in MEM contains ASC (50 ug/ml)/β-GP (10 mM) supplemented with DMSO, F4 (1.5 µM) or F4 (5 µM) for 16 Days. Media was replenished every 3-4 days until day 16, mineralization was determined by Alizarin Red staining. Cells were washed twice with PBS and fixed with 10% formalin for 1 hour. Fixed cell was washed twice with distilled water and stained with 2% Alizarin Red S solution (pH 4.1) in the dark for 1 hour. Stain solution was removed and washed 4 times with distilled water.

2. Results

Figure 1:
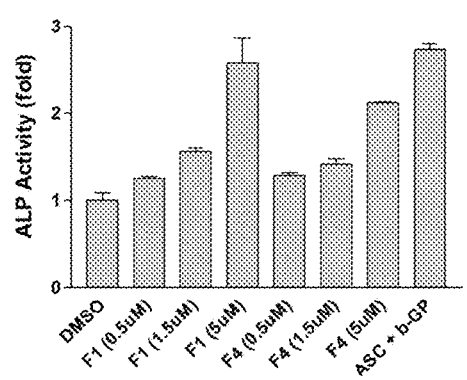
FIG. 1 is histograms showing (A) effects of F1 and F4 on ALP activity in MC3T3-E1 osteoblasts using DMSO, 0.5 µM, 1.5 µM, and 5 µM of F1, 0.5 µM, 1.5 µM, and 5 µM of F4, and ascorbate and β-glycerophosphate (ASC+b-GP)
Figure 1:
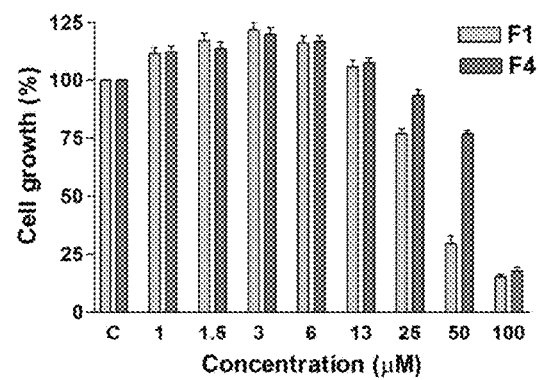

To determine whether the phenanthrenes isolated from Medulla Junci has osteogenic activity, their effects on cell differentiation and mineralization of osteoblastic MC3T3-E1 cells were first examined. As shown in FIG. 1(A), two compounds F1 and F4 increased the cellular alkaline phosphatase (ALP) enzyme activities in a concentration-dependent manner. For both compounds, the increases in ALP activities were already evident at concentrations of 0.5 µM and maximum at 5 µM at 24 and 48 h after treatment. Cells treated with 5 µM F1 or F4 showed increases in the ALP activities by 2-3 fold compared to the untreated cells. As a positive control, treatment of cells with ascorbate and β-glycerphosphate also increased the ALP activity by 2-3 fold. Furthermore, the effects of F1 and F4 on cell number were assessed by NBB assay (FIG. 1(B)). The results showed that F1 and F4 slightly increased the cell number of cell proliferation at the concentrations that stimulated ALP activities (0.625 to 10 µM). At higher concentrations (25-100 µM), significant loss of cell viability was observed.

To examine whether F1 and F4 induced functional osteoblastic differentiation, the deposition of calcified bone matrix was examined by Alizarin Red staining. MC3T3-E1 osteoblast cells were treated with F1 or F4 (at 1.5 µM or 5 µM) in osteoblast mineralization medium for 14 days, and the calcium deposition in the cell layer was measured by Alizarin Red staining. Both F1 and F4 significantly enhanced the Alizarin Red staining in MC3T3-E1 cell layers when compared with that in the control observed at day 14. More calcium deposition was observed at the higher concentration (i.e., 5 µM) of F1 or F5 than at their lower concentrations (i.e., 1.5 µM).

Example 2: Induction of Osteoblastic Differentiation-Associated Marker Genes

1. Methods and Materials

RNA Extraction and Quantitative Real-Time Polymerase Chain Reaction (Real-Time PCR)

MC3T3-E1 cells were seeded in 6-well plates at 1×10$^5$ cells per well for 2 days. Cells were treated with 0.05% DMSO, 30 ng/ml BMP2, 400 µM ASC/5 mM β-GP in MEM. Total RNA was isolated at Day 2 and Day 4 with Trizol® reagent, 1 ug of total RNA was subjected to reverse transcription/cDNA synthesis using Superscript III first-strand synthesis system (Life Technologies).

Equal amount of cDNA generated from reverse transcription reactions were subjected to real-time PCR with SYBR® Green PCR Master Mix and primers for osteoblast differentiation markers. Primers used included:

```
Alkaline phosphatase (ALP):
(forward)
                                        (SEQ ID NO: 1)
5'-TCAGGGCAATGAGGTCACATC-3'

(reverse)
                                        (SEQ ID NO: 2)
5'-CACAATGCCCACGGACTTC-3';

Osteocalcin (OCN):
(forward)
                                        (SEQ ID NO: 3)
5'-GCAATAAGGTAGTGAACAGACTCC-3'

(reverse)
                                        (SEQ ID NO: 4)
5'-GTTTGTAGGCGGTCTTCAAGC-3';

Osteropontin (OPN):
(forward)
                                        (SEQ ID NO: 5)
5'-GATGCCACAGATGAGGACCTC-3'

(reverse)
                                        (SEQ ID NO: 6)
5'-CTGGGCAACAGGGATGACAT-3';

GAPDH:
(forward)
                                        (SEQ ID NO: 7)
5'-TGGTGCTGCCAAGGCTGTGG-3'

(reverse)
                                        (SEQ ID NO: 8)
5'-TCTCCAGGCGGCACGTCAGA-3'
```

Osteoblast differentiation markers genes expression were analyzed by ABI prism 7900HT Sequence Detection System and the relative level of transcript expression was quantified by ΔΔCt method.

2. Results

The effects of F1 and F4 on the mRNA expression of the terminal differentiation markers and signaling molecules were investigated (Table 1). The terminal differentiation markers include ALP and several extracellular matrix or secreted proteins (osteocalcin, osteoportin, osteonectin, bone sialoprotein, and collagen 1A1). Among these proteins, the levels of osteocalcin (OCN) and osteoportin (OPN) were markedly increased upon treatment of cells with F1 or F4 (FIGS. 2(B, C)).

TABLE 1

Levels of mRNA expression of molecules related to osteogenesis (fold changes relative to DMSO control, normalized to GAPDH) in MC3T3-E1 osteoblast.

|  | BMP2 (30 ng/ml) | | ASC(400 µM) + β-GP (5 mM) | | F1 (5 µM) | | F4 (5 µM) | |
| --- | --- | --- | --- | --- | --- | --- | --- | --- |
|  | D 2 | D 4 | D 2 | D 4 | D 2 | D 4 | D 2 | D 4 |
| ALP | 4.2 | 2.6 | 4.4 | 4.3 | 1.8 | 2.9 | 2.1 | 4.6 |
| OCN | 13.2 | 4.8 | 4.4 | 3.7 | 29 | 11 | 17 | 9 |
| OPN | 0.8 | 1.0 | 0.7 | 1.6 | 1.4 | 1.8 | 1.5 | 2.7 |
| OSN | 1.5 | 1.9 | 1.0 | 2.3 | 0.7 | 1.6 | 0.9 | 2 |
| BSP | 2.1 | 2.0 | 4.7 | 3.6 | 2.1 | 1.3 | 1.6 | 1.2 |
| COL1A1 | 1.4 | 1.2 | 2.0 | 2.3 | 0.7 | 0.9 | 1.0 | 1.2 |
| Wnt3A | 2.4 | 6.3 | 1.1 | 20.3 | 0.9 | 2.8 | 0.9 | 1.9 |
| Wnt5A | 1.6 | 1.0 | 1.0 | .04 | 0.8 | 0.6 | 1.0 | 0.8 |
| Wnt7B | 1.5 | 1.4 | 1.0 | 2.3 | 0.8 | 1.1 | 0.6 | 0.1 |
| Wnt11 | 3.0 | 1.9 | 0.9 | 0.5 | 1.1 | 0.6 | 0.8 | 0.4 |
| Fzd1 | 6.3 | 4.4 | 12.7 | 6.3 | 3.0 | 2.6 | 3.3 | 5.8 |
| Fzd2 | 1.3 | 1.1 | 1.1 | 1.2 | 1.0 | 0.7 | 0.8 | 0.8 |
| Fzd5 | 1.9 | 1.4 | 1.1 | 0.9 | 0.8 | 0.6 | 0.7 | 0.8 |
| LRP5 | 1.0 | 0.9 | 0.9 | 0.9 | 0.8 | 0.6 | 0.9 | 1.0 |
| Axin2 | 1.9 | 3.3 | 3.4 | 2.6 | 0.9 | 1.0 | 1.1 | 1.1 |
| BMP2 | 2.7 | 0.9 | 0.9 | 5.8 | 1.2 | 0.7 | 1.0 | 0.9 |
| BMP7 | 2.8 | 1.4 | 1.1 | 1.1 | 1.6 | 1.1 | 1.0 | 1.3 |
| Runx2 | 3.0 | 2.0 | 2.1 | 1.8 | 1.1 | 1.2 | 1.3 | 1.7 |
| OSX | 3.1 | 1.9 | 0.9 | 0.7 | 0.6 | 0.5 | 0.6 | 0.6 |

TABLE 1-continued

Levels of mRNA expression of molecules related to osteogenesis (fold changes relative to DMSO control, normalized to GAPDH) in MC3T3-E1 osteoblast.

| | BMP2 (30 ng/ml) | | ASC(400 μM) + β-GP (5 mM) | | F1 (5 μM) | | F4 (5 μM) | |
|---|---|---|---|---|---|---|---|---|
| | D 2 | D 4 | D 2 | D 4 | D 2 | D 4 | D 2 | D 4 |
| ATF3 | 0.8 | 0.7 | 0.2 | 0.1 | 0.8 | 1.0 | 0.7 | 0.9 |
| AFT6 | 1.7 | 2.1 | 1.8 | 1.5 | 1.5 | 1.0 | 1.5 | 2.1 |
| VDR | 1.4 | 1.3 | 2.0 | 1.1 | 0.9 | 0.5 | 2.1 | 1.6 |

ALP—Alkaline phosphatase;
OCN—Osteocalcin;
ATF3—Activating transcription factor 3;
ATF6—Activating transcription factor 6;
OSN—Osteonectin;
Axin2—Axin-related protein 2;
OSX—Osterix;
BSP—Bone Sialoprotein;
Runx2—Runt-related transcription factor;
BMP2—Bone morphogenetic protein 2;
Wnt3A—Wnt ligand 3A;
BMP7—Bone morphogenetic protein 7;
Wnt5A—Wnt ligand 5A;
COL1A1—Collagen 1A1 (collagen, type I, alpha 1);
Wnt7B—Wnt ligand 7B;
Fzd1—Frizzled 1;
Wnt11—Wnt ligand 11;
Fzd2—Frizzled 2;
VDR—Vitamin D receptor;
Fzd5—Frizzled 5.

The signaling molecules associated with osteoblastic differentiation include Wnt ligands, Wnt receptor complexes (frizzled, LRP5), β-catenin regulator (Axin2), bone morphogenic protein (BMPs) and transcriptional regulators (runx2 and osterix) (Canalis E, Nat Rev Endocrinol. 9, 575-83 (2013); Lin G L et al., J Cell Biochem. 112, 3491-501 (2011); Komori T, J Cell Biochem. 112, 750-5 (2011)). The notable changes mediated by F4 treatment were the increases in two members of the Wnt pathway, Wnt3A and frizzled 1 (FIGS. 2(D, E)). The prototypical osteoblastic differentiation agents ascorbate/β-glycerophosphate and BMP-2 showed different gene regulation compared to the F1 and F4 compounds.

Example 3: Role of MAP Kinases in the F4 Induced ALP Activity

1. Methods and Materials
Western Blot
MC3T3-E1 were lysed with 20 mM Tris pH8.0, 137 mM NaCl, 2 mM EDTA, 1% Triton X-100 and 10% Glycerol with protease inhibitor cocktail (Roche, complete). Protein concentration was determined by Bradford Protein Assay (Bio-Rad) and equal amount of proteins (30 μg) was resolved by SDS-PAGE and transferred onto PVDF membrane. The membrane was blocked with 3% BSA in Tris-buffered saline containing 0.1% Tween 20 and incubated with primary antibody (1:1000) overnight at 4° C. then incubated with HRP-linked secondary antibody for 1 h. Chemiluminescence signals were detected using enhanced chemiluminescence reagents (GE Healthcare) on X-Ray films (Fujifilm).
2. Results
MAP kinases (ERK, p38, JNK) have been shown to be involved in the osteoblastic differentiation (Greenblatt M B et al., Annu Rev Cell Dev Biol. 29, 63-79 (2013)). To examine the roles of MAP kinases in the F4-induced osteoblastic differentiation, the effects of individual MAP kinase inhibitors on ALP activity were determined in MC3T3-E1 osteoblasts. Cells were treated with DMSO vehicle, 5 μM F4 in the presence or absence of p38 inhibitor SB203580 for 15-30 min. The levels of phosphorylated p38 and total p38 were determined by immunoblotting experiments. MC3T3-E1 osteoblasts incubated with 5 μM F4 for 15 min, and 30 min showed increased levels of phosphorylated p38. However, addition of p38 inhibitor SB203580 reduced the levels of phosphorylated p38 at either time point.

Cells were treated with DMSO vehicle or 5 μM F4 in the presence or absence of p38 inhibitor SB203580 for 2 days and the ALP activities were determined (FIG. 3). The p38 inhibitor SB203580 significantly inhibited the F4-induced increases in ALP activity, while ERK and JNK inhibitors had no appreciable effect. F4 was also shown to stimulate the phosphorylation of p38 as revealed by immunoblotting.

Example 4: F4 as Osteogenic Phytoestrogen

1. Methods and Materials
Transient Transfections and Reporter Assays
MC3T3-E1 were seeded at $9.0 \times 10^4$ per well in 24-well plates. Twenty-four hours after cell seeding, cells were transiently transfected with 500 ng pERE-Luc (contains three repeats of estrogen-response element) by lipofectamine 2000 (Life Technologies) according to manufacturers' instruction (lipofectamine:DNA=3:1). After 6 hours incubation, cells were treated with DMSO (0.05%), F4 (5 μM), or 17β-estradiol (10 nM) in MEM for 24 h.
2. Results
To gain further insight into the mechanistic action of F compounds, a chemical similarity search of F compounds based on Similarity Ensemble Approach was performed (Keiser M J et al., Nat Biotechnol. 25, 197-206 (2007)). The results are shown in Table 2. The analysis revealed that F4 was related to estrogen receptor agonist such as estradiols. This led to the investigation of the estrogen-like activities of F compounds on the osteoblastic differentiation. Using a reporter gene assay, it was shown that F4 stimulated the transcriptional activity driven by estrogen responsive gene elements (ERE) in a dose-dependent manner (FIG. 4). Importantly, the stimulatory effects could be inhibited by specific estrogen receptor antagonist (ICI182780) which also inhibited the estradiol-stimulated ERE-driven promoter activity. To determine the role of estrogen-like activity of F4 on the osteoblastic differentiation, the effect of ICI on the F4-induced ALP activity was investigated. The results showed that ICI inhibited the F4-induced activity at day 7 while no effect was observed earlier at day 4.

The results indicate that F4 stimulate estrogen receptor mediated transcriptional activity and this activities may be at least in part involved in the osteoblastic differentiation-associated ALP activity as assessed by specific estrogen receptor antagonist ICI 182780.

It has been shown for the first time that phenanthrenes isolated from Medulla Junci exhibit osteogenic effects. Two phenanthrenes compounds (F compounds, F1 and F4) were shown to stimulate differentiation of MC3T3-E1 osteoblasts at low micromolar concentrations. They markedly increased the differentiation-associated ALP enzyme activities and the mRNA expression. Furthermore, they enhanced the expression of a subset of mRNAs encoding secretory proteins associated with bone formation including OCN, OPN and OSN. Upon prolonged incubation of differentiating osteoblasts with the F compounds, there was marked stimulation of calcium mineralization. These data suggest that F compounds promote functional processes in bone formation.

TABLE 2

Chemical similarity search of F compounds based on Similarity Ensemble Approach.

| Rank | Size | Activity class | E-value | Max Tc |
|---|---|---|---|---|
| 1 | 1102 | Estrogen receptor beta [100 nM] | 5.68e−5 | 1.00 |
| 2 | 1552 | Estrogen receptor beta [1000 nM] | 2.17e−3 | 1.00 |
| 3 | 1755 | Estrogen receptor beta [10000 nM] | 5.77e−3 | 1.00 |
| 4 | 1723 | Estrogen receptor alpha [10000 nM] | 4.01e−1 | 1.00 |
| 5 | 1389 | Estrogen receptor alpha [1000 nM] | 4.78e+1 | 1.00 |
| 6 | 6 | Estrogen receptor alpha [1000 nM] | 1.75e−5 | 0.32 |
| 7 | 10 | Estrogen receptor alpha [10000 nM] | 7.11e−3 | 0.32 |
| 8 | 509 | Estrogen receptor beta [10 nM] | 2.73e−1 | 0.40 |
| 9 | 20 | Estrogen receptor beta [10 nM] | 1.73e+0 | 0.32 |
| 10 | 23 | Dopamine D1 receptor [10 nM] | 4.61e+0 | 0.31 |
| 11 | 24 | Estrogen receptor beta [100 nM] | 5.10e+0 | 0.32 |

The mechanisms of action of the F compounds were investigated by examination of gene regulations involved in osteoblastic differentiation signaling, including the pathways of Wnt (Wnt ligands, Frizzled 1, Axin2 and Lrp5), bone morphogenic proteins (BMP2, BMP7, Runx2, Osterix), and endoplasmic reticulum stress (ATF3 and ATF6) (Jang W G et al., *J Biol Chem.* 287, 905-15 (2012)). It was identified from screening these compounds that F compounds markedly upregulated the mRNA expression of two Wnt pathway members, the Wnt ligand Wnt3A and Wnt receptor frizzled 1. The canonical Wnt signaling is mediated through the binding of Wnt ligands to frizzled family of co-receptors, eventually leading to increase in nuclear β-catenin levels and transcriptional regulation of osteoblastic genes. The specific role of upregulation of frizzled 1 in the osteoblastic differentiation has been recently demonstrated (Yu S et al., *Bone.* 56, 234-41 (2013)). It was also observed that F compounds treatment increases in the ER stress related ATF6 mRNA expression. ATF6 is a transcription factor mediated unfolded protein response upon ER stress. Recently, mild ER stress induced by BMP2 was shown to positively regulates osteoblast differentiation via activation of UPR transducers including ATF6 (Jang W G et al., *J Biol Chem.* 287, 905-15 (2012)).

In summary, it has been identified that the phenanthrenes isolated from Medulla Junci are novel compounds that stimulate osteoblastic differentiation through multiple osteogenic signaling components including Wnt pathway, ER stress and estrogen receptor.

Example 5: Extracts of Medulla Junci Containing the F Compounds (Including F1 and F4) Induced Differentiation of MC3T3-E1 Osteoblasts 1. Materials and Methods Stem pith of Medulla Junci (0.5 kg) were powdered and macerated in methanol (3 L) at room temperature for three days. Herbal mixture was filtered and filtrate was dried by rotatory evaporator. The extraction procedure was repeated twice. Methanol extracts were then combined and further dried again by vacuum to get methanol extract in powder form (5 g). Before being applied in cell culture, the powdered extract was dissolved in DMSO as 10 mg/mL stock solution.

2. Results

The effects of Medulla Junci extract on MC3T3-E1 osteoblast differentiation in terms of ALP enzyme activities were examined using the procedures described in Example 1. As shown in FIG. 5, treatment of MC3T3-E1 cells with Medulla Junci extract (MJ) increased the cellular ALP enzyme activities in a concentration and time-dependent manner.

Example 6: Estrogen Receptor Binding

Quantum Mechanics/Molecular Mechanics modeling of F4 binding to estrogen receptors (ERα and ERβ) was shown in FIG. 6. The binding activity of F4 to estrogen receptors was determined by competitive radioligand estrogen receptor binding assay. The $IC_{50}$ of F4 on the estradiol binding to estrogen receptor alpha was 130 nM, and that to estrogen receptor beta was 5.6 nM (FIG. 7).

Example 7: The Effect on Estrogen Dependent Cancer Cell Proliferation

The effect of F compounds on estrogen dependent cancer cells was investigated (FIG. 8). Treatment of F4 (effusol) or F5 (dehydroeffusol) induced MCF7 cell proliferation at low dose of 0.3 µM. The fold increase of MCF7 proliferation was similar to that induced by estradiol treatment. Whereas, at dose of 5 µM or higher, both F4 and F5 inhibited the proliferation of MCF7. To further confirm the inhibitory role of F4 on MCF7 proliferation, luciferase reporter gene assay was employed (FIG. 9). It was found that F4 treatment reduced the estrogen receptor luciferase activity in a dose dependent manner in MCF7 cell that bear the estrogen receptor, but not MDA-MB-231 a breast cancer cell line that does not bear the estrogen receptor. Furthermore, treatment of both F4 and F5 could significantly suppress MCF7 cell proliferation induced by estradiol, but not that in MDA-MB-231 (FIG. 8). Collectively, all these data suggest that at dose with osteogenic effect, F4 could inhibit MCF7 cell proliferation.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising," will be understood to imply the inclusion of a stated element, integer or step, or group of elements, integers or steps, but not the exclusion of any other element, integer or step, or group of elements, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, reference to "a compound" includes a plurality of such compounds, reference to "the compound" is a reference to one or more compounds and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different components or materials does not indicate that the listed components or materials are obvious one to the other, nor is it an admission of equivalence or obviousness.

Those skilled in the art will recognize, or be able to ascertain using no more than routine experimentation, many equivalents to the specific embodiments of the method and compositions described herein. Such equivalents are intended to be encompassed by the following claims.

We claim:

1. A method for treating or preventing bone loss or promoting bone formation in a subject in need thereof, comprising: administering to the subject an effective amount of one or more of F1 and F4 (effusol), whose chemical structures are shown below respectively:

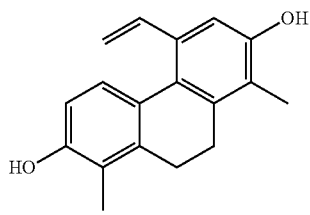

Chemical structure of F1

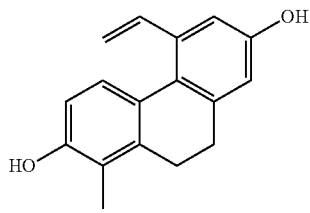

Chemical structure of F4 (Effusol)

to reduce one or more symptoms of bone loss, prevent one or more symptoms of bone loss, promote bone formation, or combinations thereof, in the subject relative to an untreated control, wherein the F1 and F4 (effusol) are either enriched at least 50-fold from natural sources, or chemically synthesized.

2. The method of claim 1, wherein F4 or effusol is used.

3. The method of claim 1, wherein the subject is human.

4. The method of claim 1, wherein the subject has osteopenia or osteoporosis.

5. The method of claim 1, wherein the one or more of F1 and F4 are administered in an amount effective to stimulate osteoblast differentiation, activity, survival, or combinations thereof, in the subject, relative to an untreated control.

6. The method of claim 1, wherein the one or more of F1 and F4 are administered in an amount effective to enhance expression of one or more osteogenic proteins relative to an untreated control.

7. The method of claim 6, wherein the one or more osteogenic proteins are selected from the group consisting of alkaline phosphatase, osteocalcin, osteoportin, osteonectin, bone sialoprotein, and combinations thereof.

8. The method of claim 1, wherein the one or more of F1 and F4 are administered in an amount effective to increase the levels of one or more osteoblast-specific transcription factors in the subject relative to an untreated control.

9. The method of claim 8, wherein the one or more osteoblast-specific transcription factors are selected from the group consisting of RUNX2, DLX5, SP7, and combinations thereof.

10. The method of claim 1, wherein the one or more of F1 and F4 are administered in an amount effective to increase phosphorylation of one or more mitogen-activated kinases (MAPKs) involved in osteoblast differentiation in the subject relative to an untreated control.

11. The method of claim 10, wherein the one or more MAPKs is p38.

12. The method of claim 1, wherein the one or more of F1 and F4 are administered in an amount effective to increase protein expression, transcript level, activity, or combinations thereof, of one or more members of the Wnt/β-catenin signaling pathway in the subject relative to an untreated control.

* * * * *